(12) United States Patent
Liao et al.

(10) Patent No.: US 11,789,259 B2
(45) Date of Patent: Oct. 17, 2023

(54) VISION INSPECTION AND CORRECTION METHOD, TOGETHER WITH THE SYSTEM APPARATUS THEREOF

(71) Applicant: PASSION LIGHT INC., Taichung (TW)

(72) Inventors: Jih-Yi Liao, Taipei (TW); Chung-Ping Chen, Taipei (TW); Tse-Yao Wang, Kaohsiung (TW); Shan-Lin Chang, Kaohsiung (TW); Ming-Cheng Tsai, Kaohsiung (TW); Chia-Hung Lin, Taipei (TW); Ter-Chin Chen, Taoyuan (TW); Chao Kai Chang, Taipei (TW)

(73) Assignee: PASSION LIGHT INC., Taichung (TW)

( * ) Notice: Subject to any disclaimer, the term of this patent is extended or adjusted under 35 U.S.C. 154(b) by 156 days.

(21) Appl. No.: 17/134,575

(22) Filed: Dec. 28, 2020

(65) Prior Publication Data
US 2022/0206291 A1    Jun. 30, 2022

(51) Int. Cl.
*G02B 27/00* (2006.01)
*A61B 3/032* (2006.01)
(Continued)

(52) U.S. Cl.
CPC ..... *G02B 27/0025* (2013.01); *G02B 27/0075* (2013.01); *H04N 13/344* (2018.05); *H04N 13/383* (2018.05); *A61B 3/0058* (2013.01); *A61B 3/02* (2013.01); *A61B 3/028* (2013.01); *A61B 3/0285* (2013.01); *A61B 3/032* (2013.01);
(Continued)

(58) Field of Classification Search
CPC ............ G02B 27/0025; G02B 27/0075; H04N 13/344; H04N 13/383; A61B 3/032; A61B 3/04; A61B 3/0025; A61B 3/08; A61B 3/02; A61B 3/028; A61B 3/0285; A61B 3/0325; A61B 3/0058; G02C 13/003;
(Continued)

(56) References Cited

U.S. PATENT DOCUMENTS

| 3,240,548 | A | * | 3/1966 | Biessels | A61B 3/028 351/239 |
| 3,811,756 | A | * | 5/1974 | Apple | A61B 3/04 351/222 |

(Continued)

*Primary Examiner* — Douglas M Wilson
(74) *Attorney, Agent, or Firm* — BACON & THOMAS, PLLC

(57) ABSTRACT

A vision inspection and correction method, which uses an image adjustment software/device to separate the eyes of the inspected person on an independent display screen, and the visual mark seen by the same vision is designed to be misaligned; through the guidance and interaction of the inspector and the inspected person, the inspector can adjust the image operation to zoom in or out, shift, focus, diverge, and rotate, etc., so that the inspected person's binocular images can be clearly distinguished and adjusted. Then, the binocular images are aligned, and the inspector will implant the correction parameters during the image adjustment process into 3D projectors, VR (virtual reality), AR (augmented reality device), MR hybrid reality device and other equipment to adjust the binocular digital image parameters, so users have, or can provide to a lens maker, personalized adjustment for comfortable images of both eyes.

9 Claims, 27 Drawing Sheets

(A)

(B)

(51) Int. Cl.
  *G02C 13/00*      (2006.01)
  *A61B 3/08*       (2006.01)
  *A61B 3/028*      (2006.01)
  *A61B 3/02*       (2006.01)
  *G02C 7/02*       (2006.01)
  *G01J 1/04*       (2006.01)
  *A61B 3/00*       (2006.01)
  *H04N 13/344*     (2018.01)
  *H04N 13/383*     (2018.01)
  *A61B 3/04*       (2006.01)

(52) U.S. Cl.
  CPC .............. *A61B 3/0325* (2013.01); *A61B 3/04* (2013.01); *A61B 3/08* (2013.01); *G01J 1/0462* (2013.01); *G02C 7/024* (2013.01); *G02C 7/025* (2013.01); *G02C 7/028* (2013.01); *G02C 13/003* (2013.01)

(58) Field of Classification Search
  CPC ........ G02C 7/024; G02C 7/025; G02C 7/028; G01J 1/0462
  See application file for complete search history.

(56) References Cited

U.S. PATENT DOCUMENTS

| | | | |
|---|---|---|---|
| 4,407,571 A * | 10/1983 | Augusto | A61B 3/02 351/243 |
| 5,557,459 A * | 9/1996 | Samson | G02B 27/0172 348/E13.059 |
| 5,825,340 A * | 10/1998 | Torizuka | G02B 27/017 348/E13.044 |
| 6,149,275 A * | 11/2000 | O'Shea | A61B 3/04 351/233 |
| 9,968,253 B2 * | 5/2018 | Lindig | A61B 3/04 |
| 10,628,942 B2 * | 4/2020 | Manela | A61B 3/14 |
| 2004/0100617 A1 * | 5/2004 | Abitbol | A61B 3/028 351/205 |
| 2007/0200927 A1 * | 8/2007 | Krenik | A61B 3/0033 348/47 |
| 2012/0108328 A1 * | 5/2012 | Konno | H04N 13/398 463/31 |
| 2012/0176482 A1 * | 7/2012 | Border | H04N 13/344 348/51 |
| 2013/0027668 A1 * | 1/2013 | Pamplona | A61B 3/032 351/239 |
| 2013/0253891 A1 * | 9/2013 | Inoue | A61B 3/028 703/6 |
| 2015/0208914 A1 * | 7/2015 | Love | A61B 3/032 351/239 |
| 2016/0048038 A1 * | 2/2016 | Ho | G02B 27/0172 351/159.76 |
| 2017/0000329 A1 * | 1/2017 | Samec | G06T 19/006 |
| 2017/0265738 A1 * | 9/2017 | Keita | A61B 3/103 |
| 2018/0136486 A1 * | 5/2018 | Macnamara | G16H 50/20 |
| 2018/0263488 A1 * | 9/2018 | Pamplona | A61B 3/0041 |
| 2019/0082951 A1 * | 3/2019 | Merriam | A61B 3/032 |
| 2020/0375454 A1 * | 12/2020 | Komurata | A61B 3/113 |
| 2021/0044789 A1 * | 2/2021 | Zavoyskikh | H04N 13/122 |
| 2021/0085173 A1 * | 3/2021 | Krall | A61B 3/08 |
| 2021/0089118 A1 * | 3/2021 | Jaeken | G02B 27/0172 |
| 2022/0171190 A1 * | 6/2022 | Trisnadi | H04N 13/337 |

* cited by examiner (A)            (B)

(4A)

a  b (4B)

(4C)

VISION INSPECTION AND CORRECTION METHOD, TOGETHER WITH THE SYSTEM APPARATUS THEREOF

FIELD OF THE INVENTION

The present invention relates to a visual inspection and correction method, in particular to the use of an image adjustment software/devices, so that the designed misaligned image seen by the eyes of the inspected person can be enlarged/reduced/shifted/focused/diverged/rotated, etc., so that the eyes of the inspected person can obtain the aligned images projected on the display screen, so as to obtain the correction parameters of the eyes of the inspected person.

DESCRIPTION OF THE RELATED ART

The eye is the window of the human soul. Through the eye, the real images outside a close space can be seen, but the eye is also like many human organs, no matter it is congenital or acquired, abnormalities may occur and cause poor vision, such as defocus (nearsightedness or farsightedness) or scattered (squint or astigmatism) and other refractive errors.

There are many reasons for poor eyesight, which can be roughly divided into organ-related causes and functional problems. The former is caused by diseases of eye-related organs, which must be diagnosed and treated by a doctor; the latter is a person who can see normal images through lens correction. The present invention is focusing on the use of lenses to correct the vision of the eyes by detecting the poor vision of the eyes of people.

As illustrated in FIGS. 1 and 2, the visual image is obtained by fusion of the images obtained by the left and right eyes. If the human brain judges the image obtained by binocular viewing as (A), it can be derived from the image obtained by left eye view (B) to fuse with the image obtained by right eye view (C). If there is a refractive error in one eye, the images obtained by the two eyes may be abnormal images that are out of proportion to the left and right, that is, as shown in FIG. 2(A), the left eye sees the reduced image, and the right eye sees the normal image; or as shown in FIG. 2(B), the left eye sees a normal image, while the right eye sees a reduced image, etc.; it may even happen that the images seen by the eyes are left and right interlaced and distorted.

With the development of optical technology, the advent of lenses will undoubtedly provide a good auxiliary effect for people with abnormal eyes. A qualified optometrist has a proficient theoretical basis and years of practical experience, and can accurately measure whether the patient's eyes have refractive errors. Because there are still differences between the comprehensive refractometer and the try-on frame used in the optometry environment and the spectacles configured after the optometry procedure, it is often that the optician feels visual discomfort.

After the lenses of most corrective glasses are installed, it is necessary to adjust the optical frame through the inspected person's visual statement and the optometrist's empirical judgment until the statement of the inspected person is deemed comfortable, but on the other hand, some lenses are polished irreversible economic considerations, so that every time the inspected person changes to a new glasses, lie is often asked by the optometrist to adapt the new glasses.

In addition, digital imaging equipment such as 3D projectors, VR (virtual reality), AR (augmented reality), and MR (hybrid reality) devices are emerging in the market. Most of the users reflect that they often have headaches and dizziness when using related optical equipment. While the short lenses wearing time and other issues have also appealed to manufacturers for improvement.

It is noticed that, at present, the optometry of eyeglasses is mainly based on the relevant optometry equipment and the experience of qualified optometrists. However, the optometry equipment and trial frames used in the optometry process are the same as the lenses actually worn by the inspected person. Its optical angle design is different, it is impossible to fully predict whether it will meet the actual optical correction parameters of the inspected person.

An important thing is that, Pupillary Distance (PD) in optometry is quickly measured with an instrument. If the inspected person's vision is slightly deflected, the optometrist may not find it, then the measure data may be biased. As for the distance between the two geometric centers of the frame (Frame PD, FPD for short), it is usually determined by the frame selected by the wearer, which may affect the wearer's visual experience.

Secondly, there are two general factors for uncomfortable glasses. One is that the pupillary distance (PD) is out of axis with the optical center of the lens, which induces the prism effect; the second is the improper adjustment of the frame curvature, which causes the optical axis of the lens. The optical axis and the visual axis of the eye (visual axis) do not induce distortion effects at the same time. These two parts may not be detected due to the short process of guided optometry and the conscious perception of the inspected person's line of sight, which may cause visual discomfort after being fitted with glasses.

SUMMARY OF THE INVENTION

In view of the above, the inventors have accumulated experience and technology in the manufacture of various optical lenses. The inspectors for the above-mentioned conventional poor vision are not enough to enable the inspected person to see normal images through lens correction. The way of improvement, after continuous research and experimental improvement, finally developed the visual inspection and correction method together with the system apparatus of the present invention.

Therefore, the present invention is objected to provide a method for visual inspection and correction, which enables the majority of the inspected person with refractive errors to see the aligned normal images through lenses after refraction and spectacles. It is mainly based on the cooperation between the vision inspector and the inspected person, using a central processing system to obtain the correction parameters of the examinee's eyes at the same time. There is no need to test the eyes twice at different times, which can greatly shorten the running-in time between the eyes and the lens, so that the eyes can quickly adapt to the corrective lens.

According to the visual inspection and correction method together with system apparatus thereof of the present invention, a central processing system with image adjustment software/device is mainly used to make the misaligned image obtained by abnormal eyes can be enlarged/reduced/shifted/focused/diverged/rotated, etc., the adjustment allows the subject's eyes to project the computer screen of the system on the display screen to see the aligned image.

According to the vision inspection and correction method of the present invention, the central processing system of the image adjustment device is connected to the monitor, and the software of the image adjustment device can be adjusted by the inspector to correct the designed misalignment seen by the inspector. The image is adjusted until the image seen by the inspected person is clearly aligned with the image, and the obtained adjustment data (correction parameters) are then converted into the trimming parameters for making optical lenses. In this way, the lens manufacturer can use the trimming parameters of the lens are used to produce lens suitable for the inspected person.

According to the vision inspection and correction method of the present invention, the three-dimensional image can also be used to obtain lenses that are specially used by the tested patients with abnormal eyes to enjoy 3D projectors, VR (virtual reality), AR (Amplified reality device), MR hybrid reality device, etc.

Regarding the system apparatus of the vision inspection and correction method of the present invention, it provides a binocular vision focal length detection auxiliary device, which includes: an optical main frame is selected from one of trial frames and general glasses; when selected from the trial frame, it has two round frame parts and four lens engaging parts; the four lens engaging parts are respectively arranged on the two at least one lens is inserted on the round frame part; when selected from the general lenses, they have the two round frame parts, and each round frame part is provided with the lens; each lens is used to correspond to one of the eyes of the wearer; a pupil line of sight the measuring frame is set corresponding to the optical main frame, and the pupil sight measuring frame has a body part, two movable frame parts, two binocular vision focal length detection auxiliary devices and two first fixed parts; the body part corresponds to the two movable frame parts, and has at least one frame slot. Each movable frame part has an insertion end portion and an adjustment end portion facing each other, and the insertion end portion is provided for the movable frame is inserted into the frame slot and can be moved and adjusted relatively horizontally; the adjustment end is for the binocular vision focal length detection auxiliary device to be inserted, and can be moved and rotated relative to each other.

The binocular vision focal length detection auxiliary device has a hole corresponding to the line of sight of the two eyes. Each of the second fixing parts is screwed on the main body part, and when the corresponding movable frame part and the frame groove are moved horizontally and adjusted to position, the movable frame part is fixed by a screw lock a plurality of telescopic adjustment components are respectively pivoted between the optical main frame and the pupil sight measuring frame; each of the telescopic adjustment components follows one of the sight lines of the eyes to independently adjust the optics the distance between the main frame and the pupil line of sight measurement frame; thereby, when the line of sight of the inspected person's eyes is viewed through the at least two lenses and the two slits, an optotype can be viewed through similar to the calculation of the triangle obtains the structure of the pupil distance of the eyes and the distance between the two geometric centers of the two circular frames; a plurality of telescopic adjustment components are respectively pivoted between the optical main frame and the pupil sight measuring frame; each of the telescopic adjustment components follows one of the sight lines of the eyes to independently adjust the optics distance between the main frame and the pupil line of sight measurement frame; thereby, when the line of sight of the wearer's eyes is viewed through the at least two lenses and the two slits, an optotype can be viewed through similar calculation of the triangle obtains the structure of the pupil distance of the eyes and the distance between the two geometric centers of the two circular frames.

As for the detailed constitution, application principle, function and effect of the present invention, please refer to the following description in accordance with the accompanying drawings to get a complete understanding.

PREFERRED EMBODIMENT OF THE PRESENT INVENTION

Figure 3:
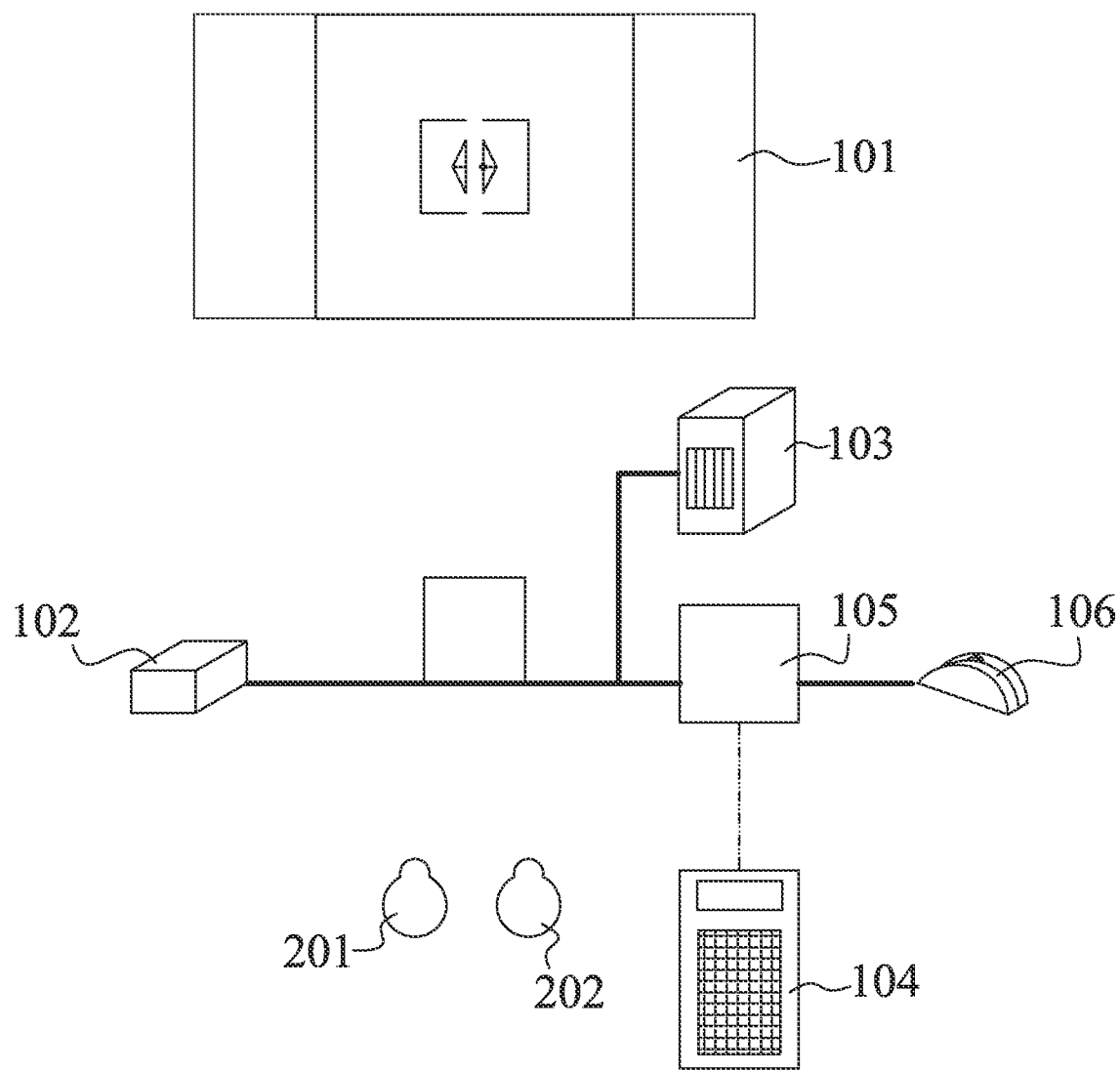
FIG. 3 is a system diagram of the visual inspection and correction method of the present invention.

The vision inspection and correction method of the present invention includes two inspected processes and systems, the first one is an images fusion process, the second one is a binocular vision focal length detection process; wherein, the first one mainly uses an image adjustment software/device, so that the misaligned image seen by the inspected person's abnormal eyes can be enlarged/reduced/shifted/focused/diverged/the adjustment of rotation, etc., enables the eyes of the subject to be inspected person on the display surface to obtain an alignment image. The implementation process and system are as follows:

As shown in FIG. 3, the first process of the visual inspection and correction method of the present invention utilizes the following facilities:

(1) Display screen 101: used to display images, so that both eyes 201 and 202 of the subject can see the fusion image seen by the convergent subject with a single eye and separated images on the display screen 101.

(2) Projection device 102: It is connected to a central processing unit (CPU) 103, and receives the image files stored in the central processing unit, and projects the image onto the display screen 101.

Figure 1:
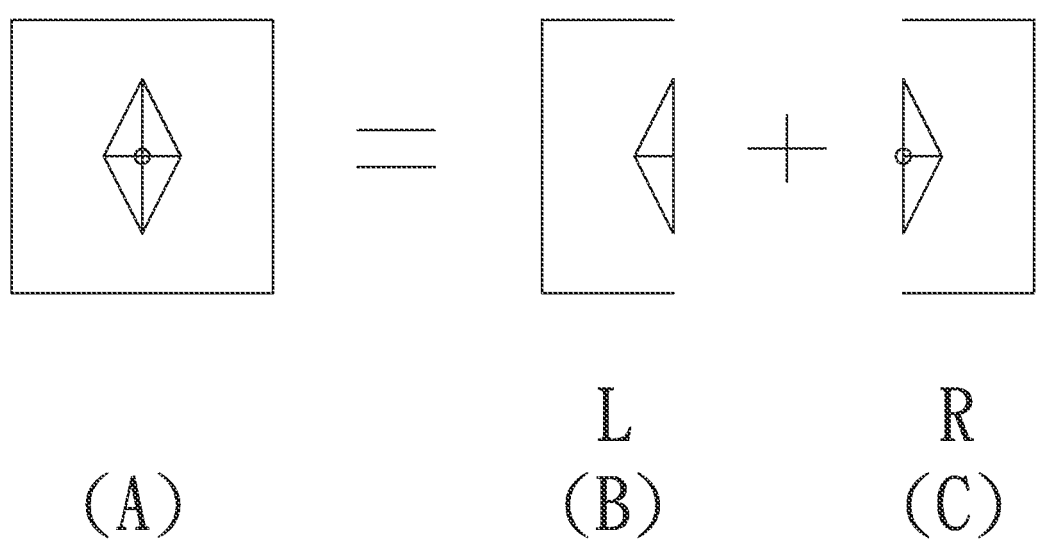
FIG. 1 is a schematic diagram of normal human binocular fusion imaging.
Figure 4:
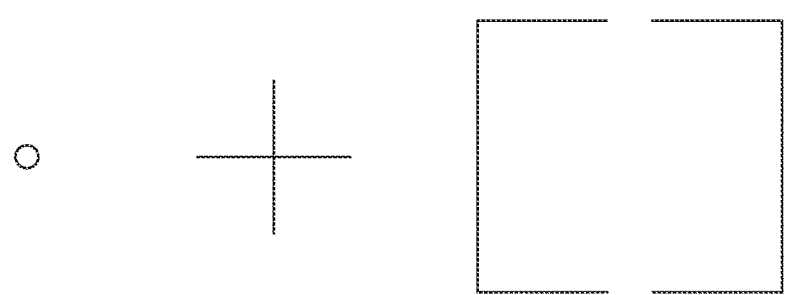
FIG. 4 is an example diagram of stored images of the central processing unit of the visual inspection and correction method of the present invention.
Figure 4:
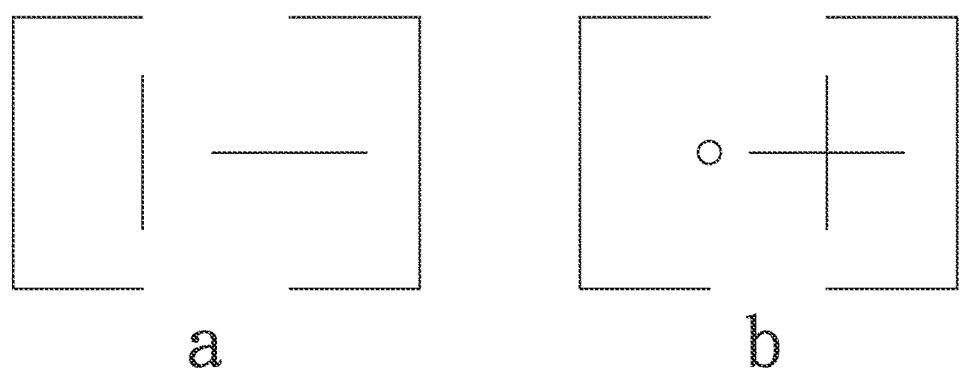
Figure 4:
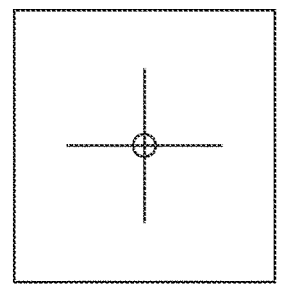

The image stored in the central processing unit (CPU) 103 has an independent three-dimensional image, including images of points, lines, and surfaces, as shown in FIG. 4A to 4C. There are two separate images on the left and right, and a subject with normal eyes can see the aligned fusion image on the display screen (such as FIG. 1A or FIG. 4C) by using both eyes 201 and 202 at the same time; Using monocular 201 or 202, the image you see is half of the image (such as FIGS. 1B, 1C or FIG. 4B).

(3) The remote control 104: It is used to control the on/off of the projection device 102, the projected image is mutated due to the enlargement/reduction/shift/focus/divergence/rotation made by receiving the instructions of the examinee, and the above-mentioned changes of the image The variable is stored in the central processing unit (CPU) 103 in a numerical manner and converted into a parameter. The remote control 104 can also be replaced or added by the monitor 105 and the keyboard 106 (mouse).

In the first process of the visual inspection and correction method of the present invention, the implementation steps are as follows:

Step 1: Project the image input by the projection device 102 from the central processing unit (CPU) 103 to the display screen 101; the image is a combination of two halves of the image, which is for the subject with normal eyes in terms of seeing an aligned fusion image.

Step 2: If the image seen by the subject's eyes is a non-aligned fusion image, the subject is asked to look at the image with a single eye one by one, and use the remote control 104 or keyboard (mouse) 106 zoom in or zoom out the images one by one: shift left/right or up/down; focus or diverge; turn left/right; turn up/down, etc., until the subject's eyes see The image is up to the aligned fusion. At this time, the central processing unit (CPU) 103 has recorded the image data adjusted by the subject. At this time, the image displayed on the monitor 105 is not actually a fusion image of the alignment.

Step 3: The adjusted data obtained in step 2 is the correction parameter, and the correction parameter is sent to the glasses factory to produce glasses suitable for the subject to wear.

Figure 5:
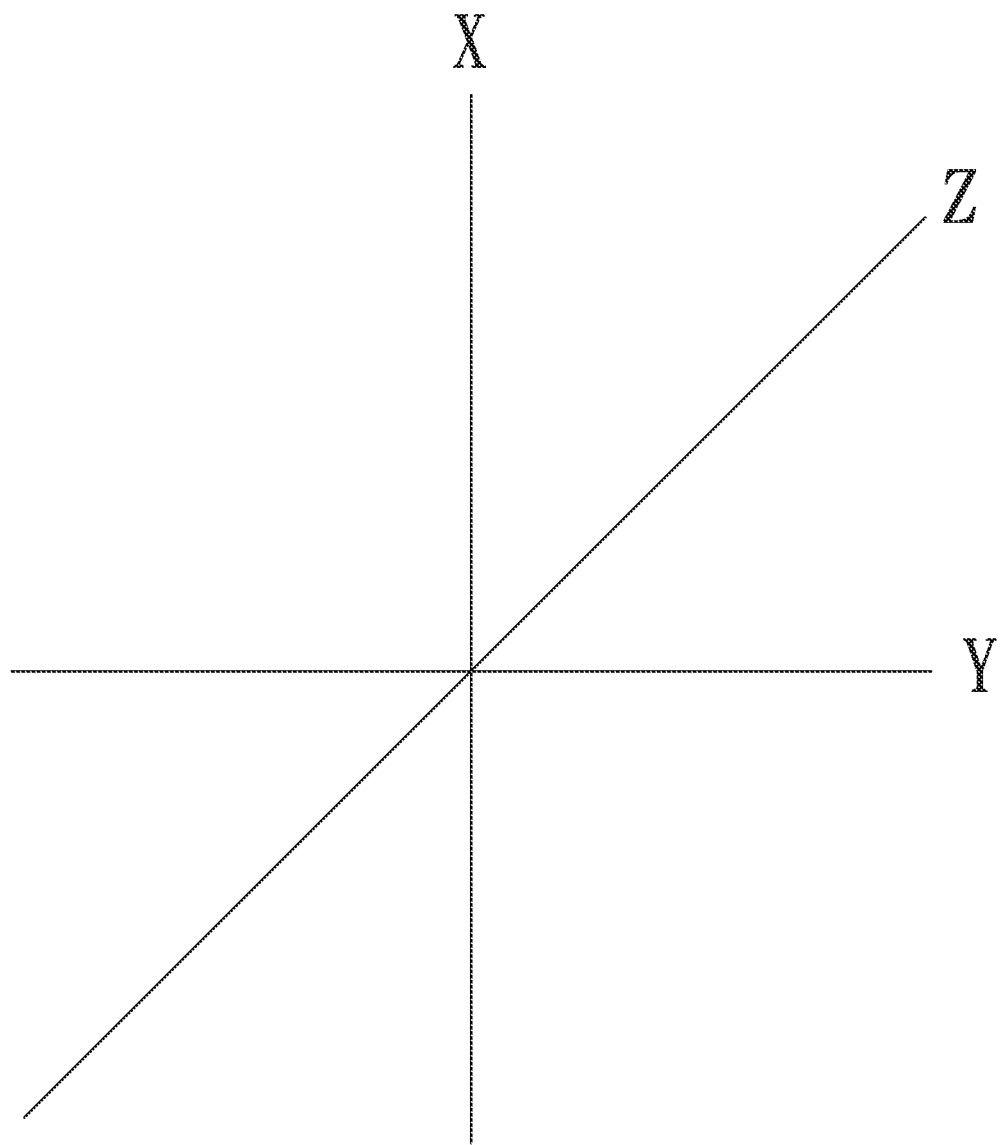
FIG. 5 is a schematic diagram of the X, Y, and Z axes of the vision detection and correction method of the present invention applied to 3D image correction.

The first process of the visual detection and correction method of the present invention described above is presented in a two-dimensional manner. In fact, the present invention can also be implemented in a three-dimensional manner. The steps are as follows:

A. Use a binocular image separation device such as AR (augmented reality) mirror device, MR (mixed reality) device, binocular image separation projection device, etc. that can see different images on the X, Y, and Z axes simultaneously (as shown in FIG. 5).

Figure 6:
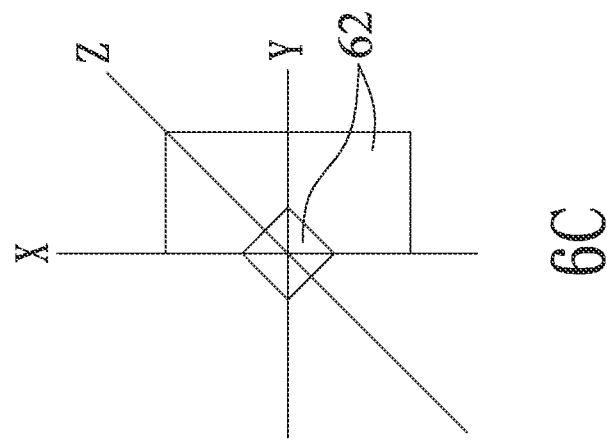
FIG. 6 is an explanatory diagrams of the X and Y-axis fusion test of the vision detection and correction method of the present invention implemented in 3D image correction.
Figure 6:
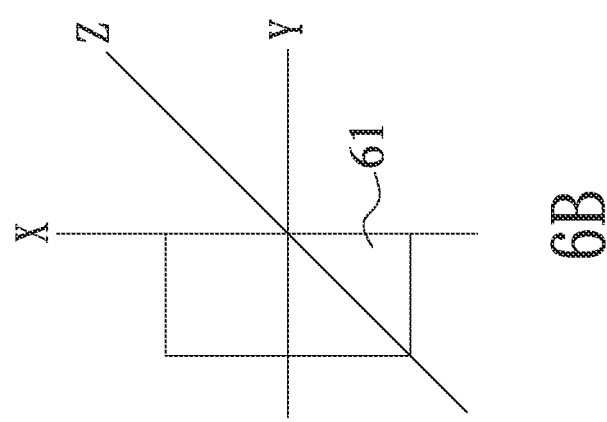
Figure 6:
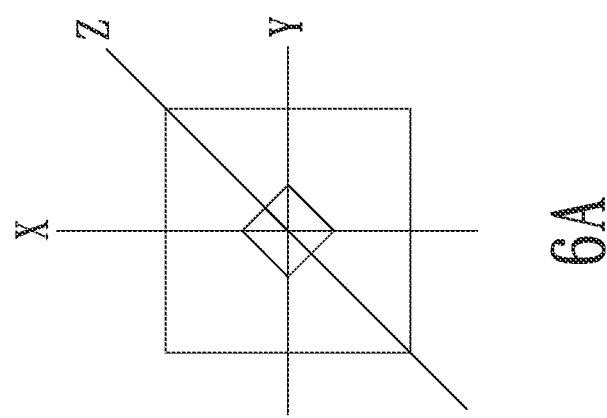

B. The XY-axis fusion test of X, Y, and Z axes, use the independent imaging method of both eyes to let the left eye look at the red mark 61 (as shown in FIG. 6B) and the right eye to look at the blue mark 62 (as shown in FIG. 6C), then use a regulator to adjust the size of the X-axis of non dominant eye to conform with the size to the X-axis of dominant eye; then rotate the optomark 90 degrees around the Z axis to adjust the size of Y-axis of non dominant eye to conform with the size of the Y-axis of dominant eye, thus the image difference parameters of the XY axis of the inspected person's eyes can be obtained.

Figure 7:
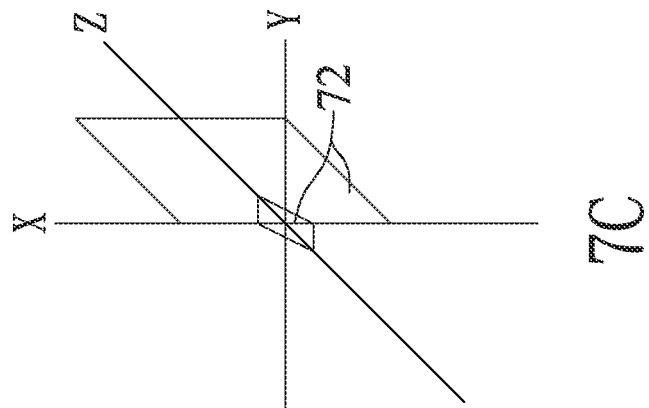
FIG. 7 is an explanatory diagrams of the X and Z-axis fusion test when the vision detection and correction method of the present invention is implemented in 3D image correction.
Figure 7:
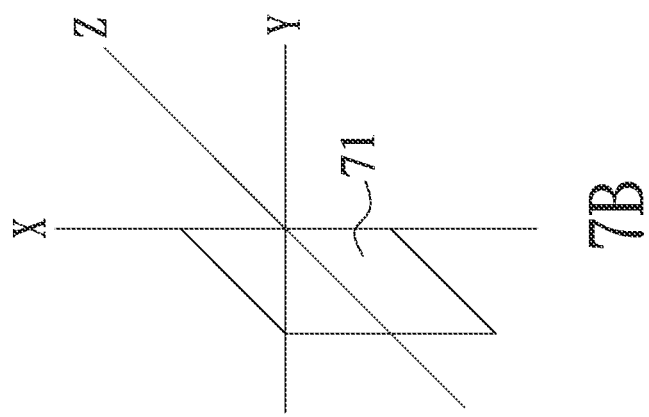
Figure 7:
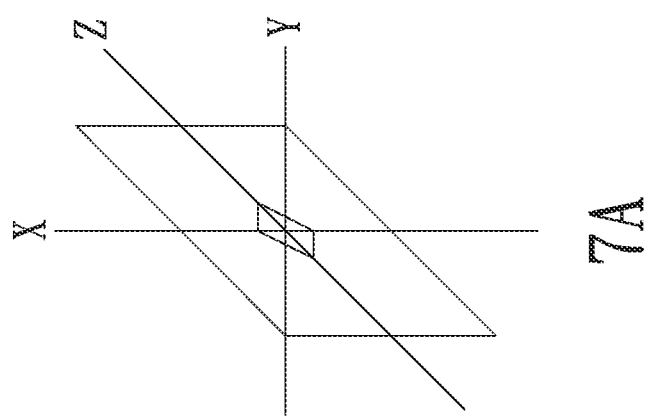

C. The XZ axis fusion test of X, Y, and Z axes, use the binocular independent imaging method to allow the left eye to look at the red mark 71 (as shown in FIG. 7B) and the right eye to look at the blue mark 72 (as shown in FIG. 7C), then use a regulator to adjust the size of the X-axis of non dominant eye to conform with the X-axis of dominant eye; then rotate the optomark 90 degrees around the Y axis to adjust the size of the Z-axis of non dominant eye to conform with the size of the Z axis of dominant eye, then image difference parameters of the XZ axis of the inspected person's eyes can be obtained.

Figure 8:
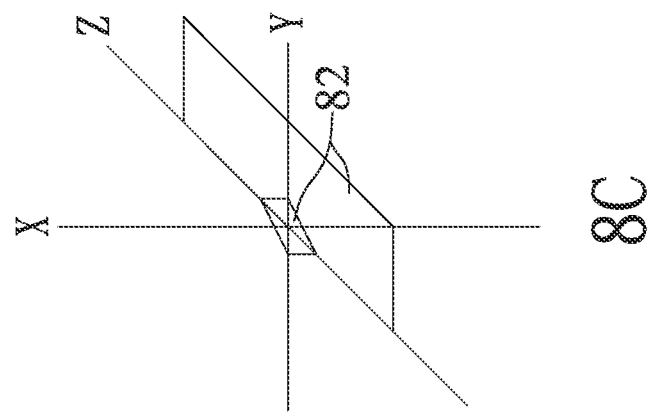
FIG. 8 is an explanatory diagrams of the Z and Y-axis fusion test when the vision detection and correction method of the present invention is implemented in 3D image correction.
Figure 8:
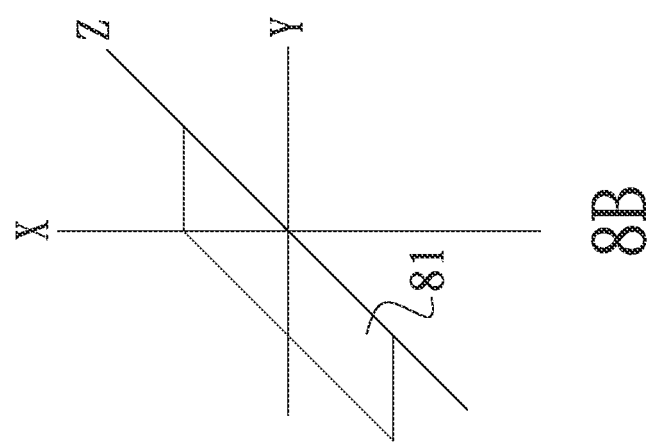
Figure 8:
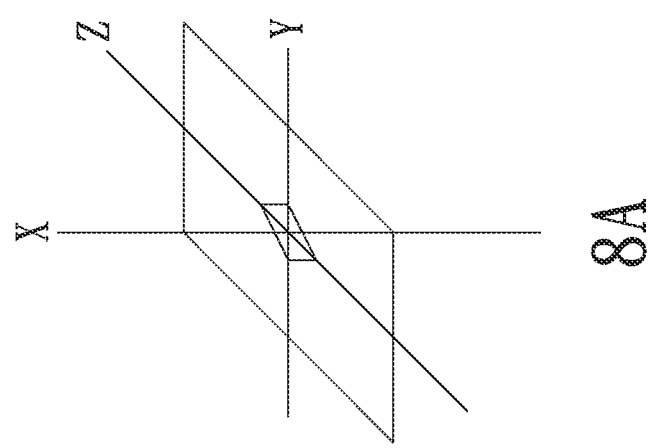

D. The ZY-axis fusion test of the X, Y, and Z axes, use the binocular independent imaging method to allow the left eye to look at the red mark 81 (as shown in FIG. 8B) and the right eye to look at the blue mark 82 (as shown in FIG. 8C), then, use a regulator to adjust the size of Z-axis of the non dominant eye to confirm with the Z-axis of dominant eye; then rotate the optomark 90 degrees around the X axis to adjust the size of Y-axis of non dominant eye to confirm with the size of the Y axis of dominant eye, thus the image difference parameters of the ZY axis of the inspected person's eyes can be obtained.

E. The XY, XZ, and ZY three-plane spatial difference parameters of the inspected person are made into a dual-eye separation imaging device, which can correct the physiological and optical errors of the human eye with the two dimensional image or three-dimensional image.

The first process of the vision detection and correction method of the present invention can detect abnormal eyesight due to congenital or acquired reasons. It is not just that ordinary optometry only checks the power of bright eyes, so that the inspected person can wear glasses with the right power. It can also obtain the parameters of the inspected person's eye abnormalities, so that the glasses manufacturers can polish the lenses to correct eye misalignment and curvature. Uncorrected abnormalities, so that the changer can get glasses with correct corrective effect; further, it can provide medical reference for ophthalmologists.

Figure 9:
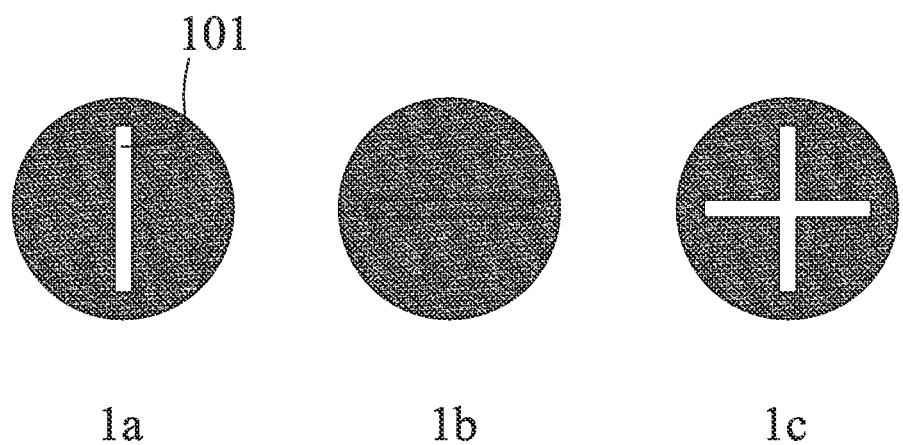
FIG. 9 is a schematic diagram of the split hole plate of the present invention.
Figure 10:
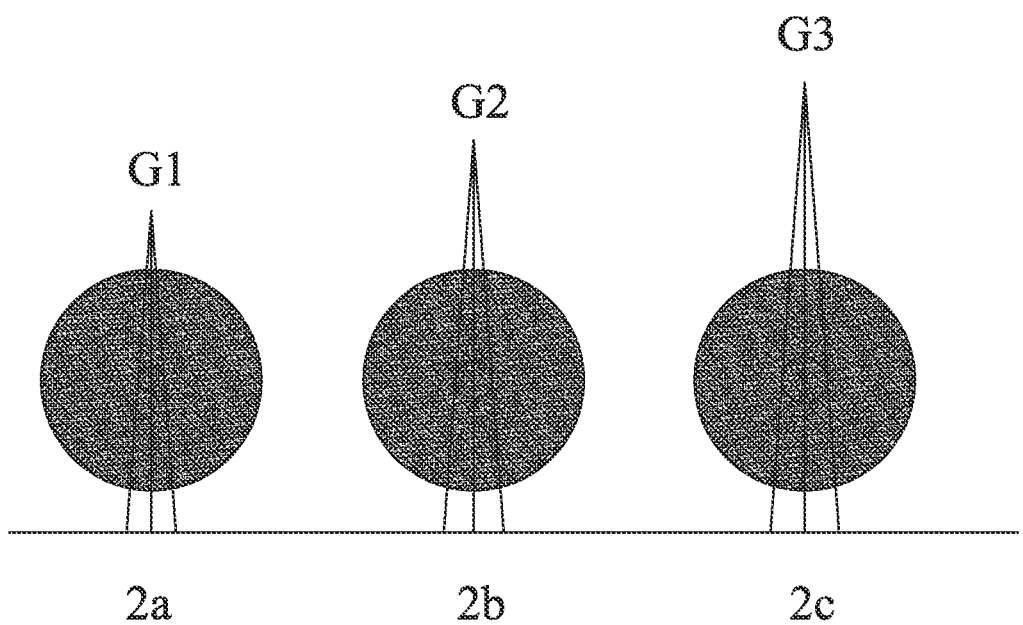
FIG. 10 is a schematic diagram of the correspondence between the size of the crack hole and the size of the prototype according to the present invention.

The second process of binocular vision focal length detection process of the present invention uses a plate with slit (hereinafter referred to as slit plate) to rotate to vertical, horizontal and horizontal positions, and the inspected person uses his own vision to move the position of the slit plate, determine the position of its visual center (as shown in FIG. 9).

In order to avoid the inspected person's own refractive errors from interfering with the measurement results, the following principles are required:
1. The subject process has to be proceeded after the inspected person completes the optometry examination, and the maximum plus to maximum visual acuity (MPMVA) of the eyes are respectively obtained.
2. Before using the slit plate, determine the errors respectively between the basic positioning of the optical center of the lens with the horizontal axis and vertical axis of the pupil center about 2 mm, so that the inspected person can quickly see the slit.
3. When using the slit plate, the corrective optical lens must be moved synchronously, and the optical center (OC) of the lens must be able to coordinate with the adjustment of the slit plate, in up, down, left and right.
4. The adjustment of the slit plate can be guided by the optometrist, or the subject can adjust it by himself. It is hoped that the final position of the slit plate can be judged by the inspected person's vision.
5. At least one slit plate is to be used.

Figure 2:
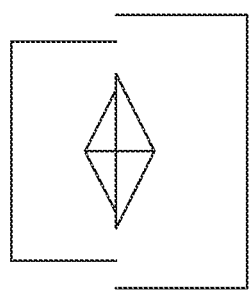
FIG. 2 is a schematic diagram of an abnormal binocular vision imaging of the human.
Figure 2:
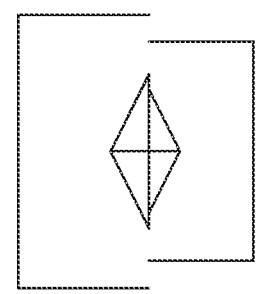

The width of the slit plate will also affect the results. The distance, middle and near vision marks (G1, G2, G3) should be matched with different distances to calculate the corresponding slit size (2*a*, 2*b*, 2*c*) and the angular vision of the same optomark, so that the visual size of the subject at different measurement positions is consistent and assists the inspected person a clearer judgment (as shown in FIG. 2).

Figure 11:
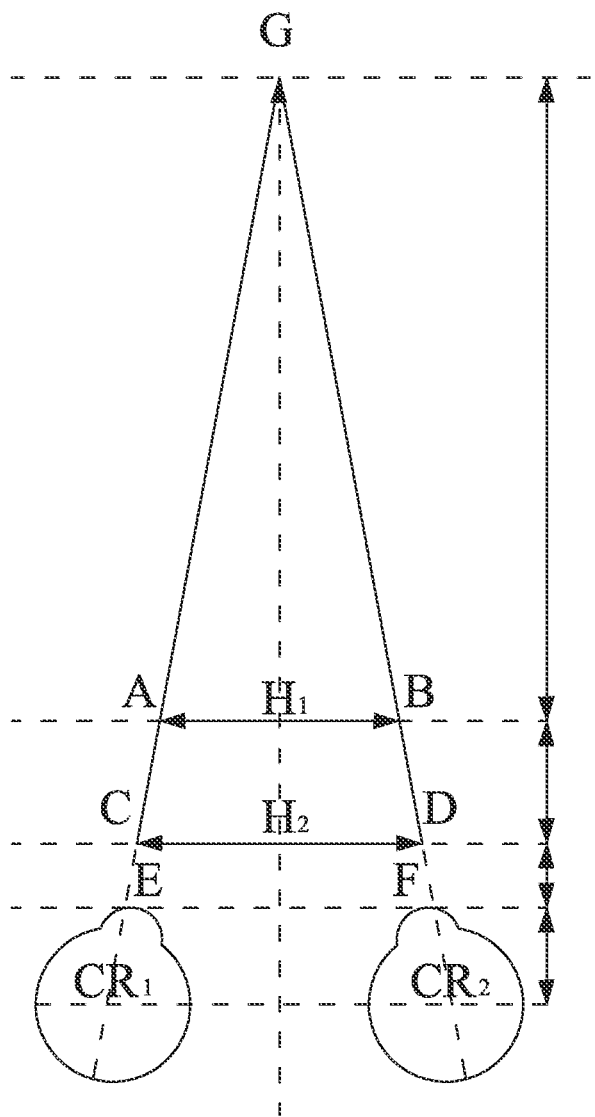
FIG. 11 is a schematic diagram of the visual axis, physiological distance and relative position of the slit plate of the present invention.

The distance of the optomark (G) and the position of the slit plate (AB), the visual plane (CD), the corneal vertex (EF) can be used to calculate the visual (AC, BD) of the inspected person's eyes and the position of the physiological interpupillary distances CR1, CR2 through the similar triangles in pythagorean theorem (as shown in FIG. 11). If the three inner angles of two triangles are equal, the corresponding sides should be proportional. The formula is:

$$(GA/GC) = (AB/CD) = GH1/GH2$$

The distance measurement of the visual mid and the distance measurement of the slit-hole plate adopt digital measurement methods. The current distances for vision inspections in various ophthalmology and optometry clinics across the country are limited due to various places, so the distances are not the same, and the subjects have different influence distances due to sitting habits. In order to avoid discomfort affecting the measurement process, it is not directly erected on the inspection tool. The inspector measures the actual inspection distance during the inspection.

Figure 12:
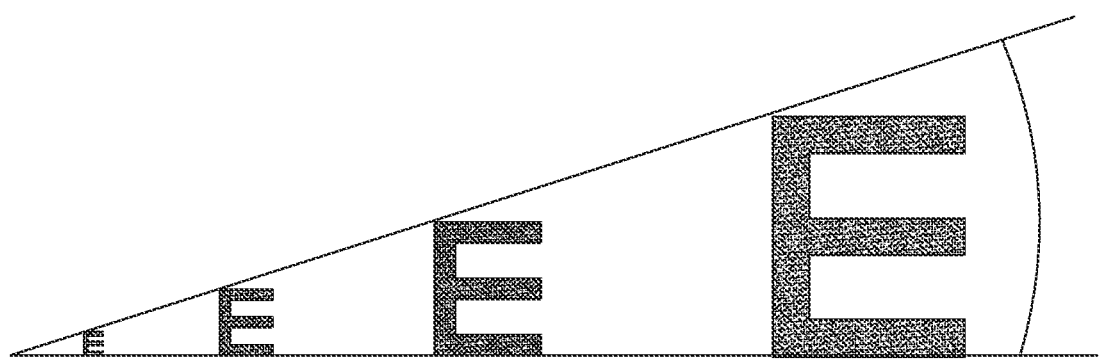
FIG. 12 is a schematic diagram of the measurement distance and the size of the optical type according to the present invention.

The basic principle of the binocular vision focal length detection auxiliary device of the present invention is:

The relationship between the conversion of the measured distance (A) of the optotype and the slit plate and the conversion of the height (D) of the optotype, as shown in Table 2.1 and FIG. 12.

Table 2.1 shows a relationship between measurement distance (A) and optomark size.

| Check distance | Visual mark setting | Visual mark size | | Visual mark frame |
|---|---|---|---|---|
| Unit: mm | Unit: VA | Unit Split angle | Unit: mm | Unit: mm |
| 400 | 0.60 | 8.33 | 0.97 | 1.94 |
| 1000 | 0.60 | 8.33 | 2.42 | 4.84 |
| 2000 | 0.60 | 8.33 | 4.84 | 9.69 |
| 3000 | 0.60 | 8.33 | 7.26 | 14.55 |
| 4000 | 0.60 | 8.33 | 9.69 | 19.39 |
| 5000 | 0.60 | 8.33 | 12.12 | 24.24 |
| 6000 | 0.60 | 8.33 | 14.55 | 29.10 |

Figure 13:
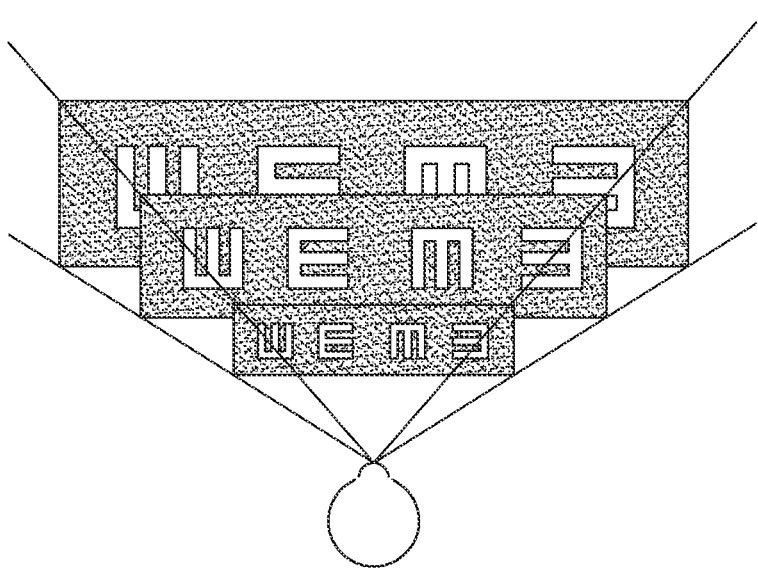
FIG. 13 is a schematic diagram of the horizontal visual target of the present invention.
Figure 14:
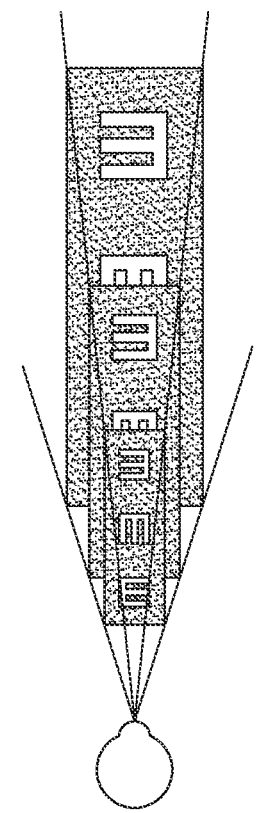
FIG. 14 is a schematic diagram of the present invention for measuring vertical visual targets.

The conversion formula and the main parameters and representative definitions for distance are as follows:
1. Measure distance. The distance between the vertex plane of the cornea and the optotype.
2. Visual mark setting. The normal vision range after correction is taken as the object of this research and development. The visual mark is set to a relative distance according to a visual acuity, for example a visual acuity of 0.6. Allow the inspected person's eyes to focus and watch easily. According to the American Medical Association (AMA) vision standard, vision greater than 0.63 is considered normal.
3. Visual mark size: 0.6 visual mark size is 8.33 minutes (5"/0.6=8.33").
4. Visual mark height: A×tan (C/60)=D
5. Visual mark frame: adopt 2 times visual mark size. The horizontal slit plate corresponds to the horizontal visual mark (as shown in FIG. 13). The vertical slit plate corresponds to the vertical visual mark (as shown in FIG. 14). The formula is: (A)×tan(C×2/60)=(E)

Figure 15:
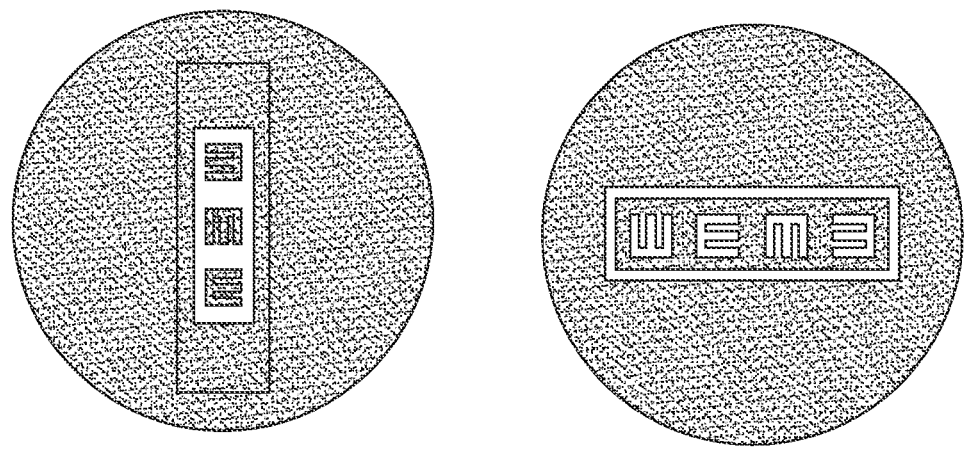
FIG. 15 is a schematic diagram of the corresponding visual standard using vertical and horizontal slit plates in the present invention.

Split plate setting. The horizontal slit plate corresponds to the horizontal visual mark, and the vertical slit plate corresponds to the vertical visual mark (as shown in FIG. 15).

Application of Optometry Timing Check:

Distance: The closer the slit plate is to the corneal vertex plane, the larger the viewing angle, and the greater the measurement error. The farther the slit plate is from the eyeball, the smaller the viewing angle and the smaller the measurement error. As shown in Table 2.2.

TABLE 2.2

The movement relation table of the slit plate

| Unit of distance from pupil: mm | Slit plate size unit: mm | Tangent unit: none | Field of view Unit: Angle | Field of view Unit: sub-angle |
|---|---|---|---|---|
| 10.00 | 1.00 | 0.1000 | 5.71 | 342.64 |
| 50.00 | 1.00 | 0.0200 | 1.15 | 68.75 |
| 100.00 | 1.00 | 0.0100 | 0.57 | 34.38 |
| 137.50 | 1.00 | 0.0073 | 0.42 | 25.00 |
| 150.00 | 1.00 | 0.0067 | 0.38 | 22.92 |

$$(A \times \tan(C \times 3/60) = E)$$

Figure 16:
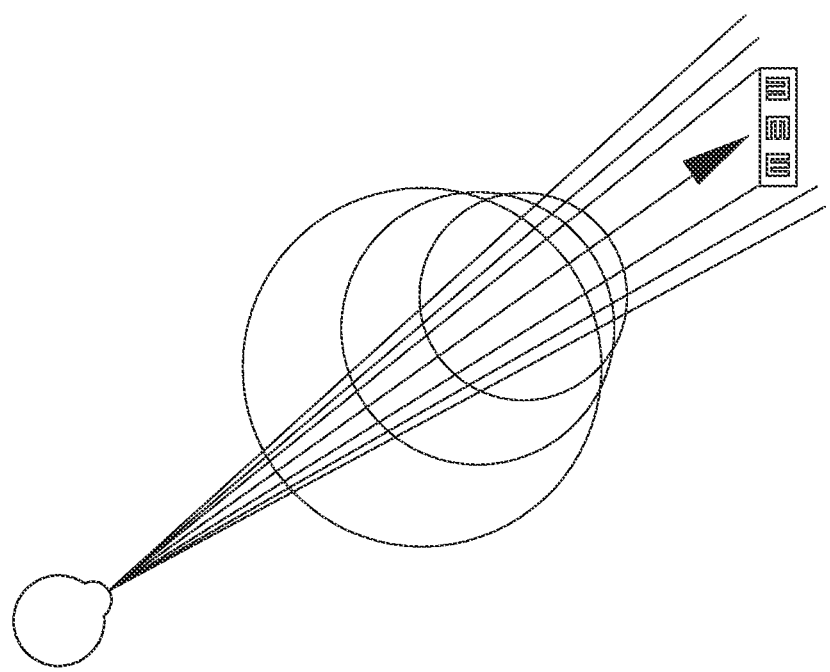
FIG. 16 is a schematic diagram of the field of view of the slit plate of the present invention at different distances.

The "zoom method" is used in the measurement. The measurement is first placed at a close distance to give the measurer a larger field of view, and the distant vision target is observed, and then gradually zoomed in to narrow the field of view to achieve measurement accuracy. The final expected field of vision is 3 times the size of the visual mark frame, which is 25 minutes, and 2 times the size of the visual mark frame, which means 16.67 minutes (as shown in FIG. 16).

Error value setting. Viewing angle=25 minutes when the slit plate is extended to 137.5 mm.

(Viewing angle 25 minutes–visual standard 16.67 minutes)/2=8.33 minutes/2.

Error value: 4.17 minute angle, which is 0.12 prism.

Figure 17:
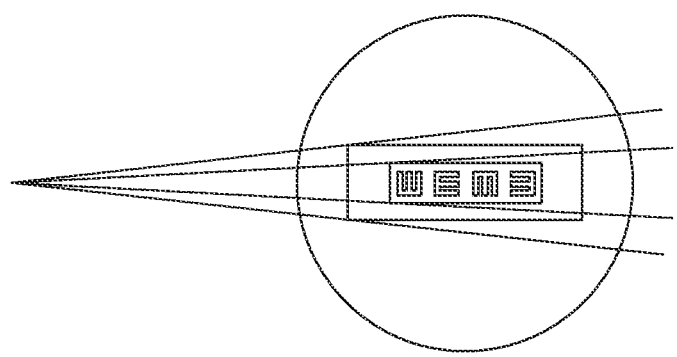
FIG. 17 is a schematic diagram of the fusion displacement drop of the present invention.

When using the slit plate, the subject may be disturbed by personal emotional factors and binocular visual fusion, or the external environment setting error, resulting in the subject's slight visual displacement when observing from the slit plate, causing errors (as shown in Table 2.3 and FIG. 17),

TABLE 2.3

The relationship between the distance, field of view, and prism of the slit plate

| Visual target distance Unit: mm | Displacement distance Unit: minute of angle | Displacement XX Unit: Δ | Tangent Unit: none | Displacement Unit: degree of angle | Displacement Unit: minute of angle |
|---|---|---|---|---|---|
| 1000 | 2.42 | 0.24 | 0.0024 | 0.14 | 8.33 |
| 1000 | 2.00 | 0.20 | 0.0020 | 0.11 | 6.88 |
| 1000 | 1.21 | 0.12 | 0.0012 | 0.07 | 4.17 |
| 1000 | 1.00 | 0.10 | 0.0010 | 0.06 | 3.44 |
| 1000 | 0.29 | 0.03 | 0.0003 | 0.02 | 1.00 |

Application after Assembly of Glasses

The assembly method and basic settings are the same as the application method of optometry inspection in Table 2, but it is necessary to consider the variables of the frame curvature (form, face) and the position of the optical center when the lens is assembled to the glasses. The visual axis overlaps the optical axis of the lens to achieve the best comfort for the wearer after the glasses are assembled.

The binocular vision focal length detection auxiliary device of the present invention has a system construction: in this study, a trial frame or full correction of optometry can be used to add a movable slit plate to the optical glasses frame, through the subject's own vision, Verify eye position and fusion of both eyes.

Figure 18:
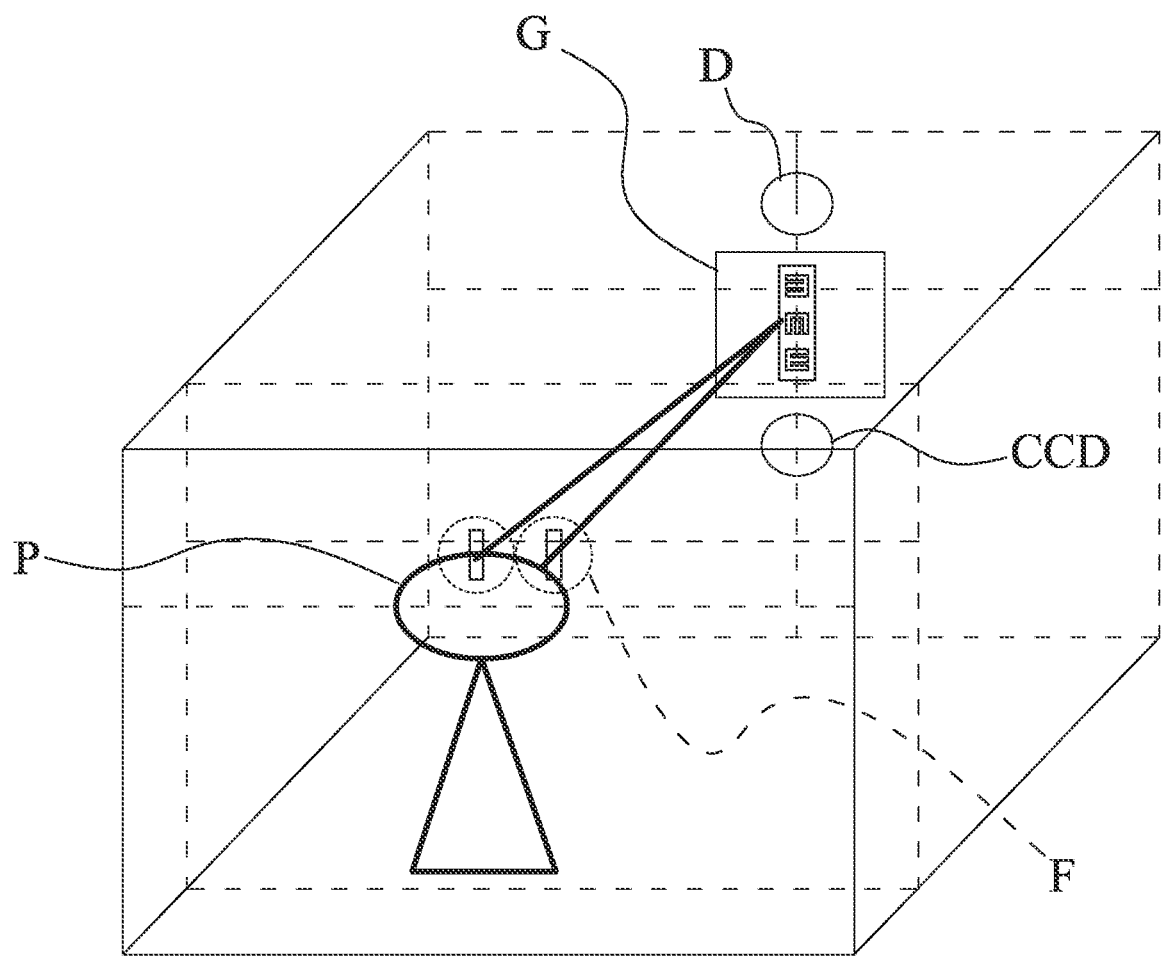
FIG. 18 is a schematic diagram of the present invention's inspection site layout.

The system construction is to put on the trial frame module in front of the testee's eyes, and the testee must complete the refraction before the pupil distance PD measurement. The system includes the subject, rangefinder module, visual target module, test frame module and CCD camera, etc. (as shown in FIG. 18).

Figure 19:
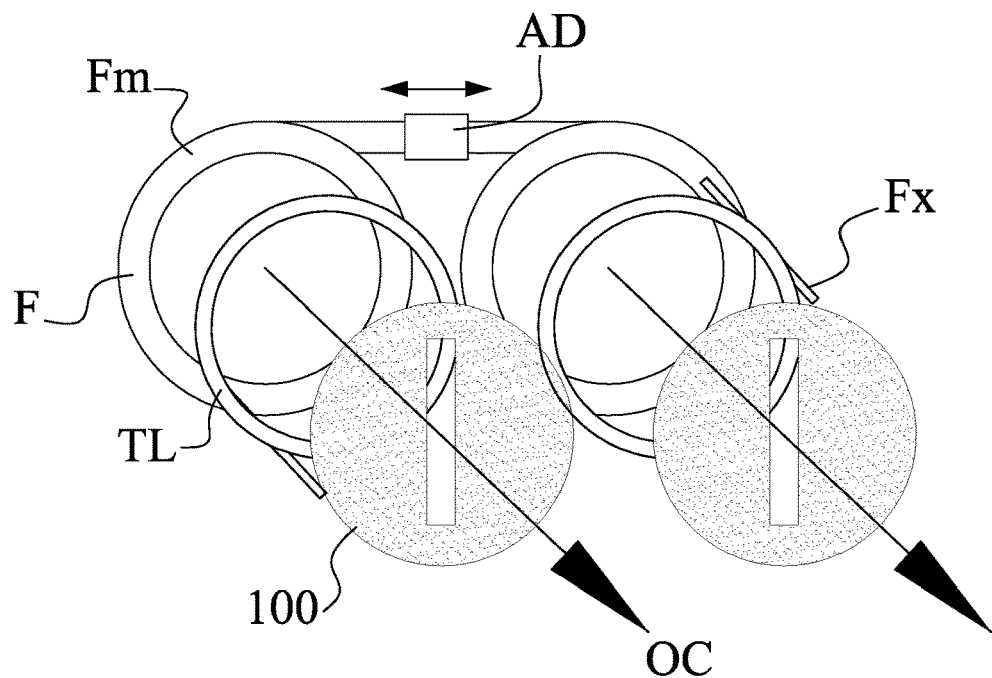
FIG. 19 is a schematic diagram of the test frame module of the present invention.

The System Module Includes:

Trial frame module F: It has a knob AD for public use and fine adjustment of the interpupillary distance (PD). Trial lenses can also be inserted to correct the refractive error of the inspected person. The slit plate 100 can be close to the corrective optics center (OC). Cooperate with the adjustment of the slit plate to up, down, left and right (as shown in FIG. 19).

Figure 20:
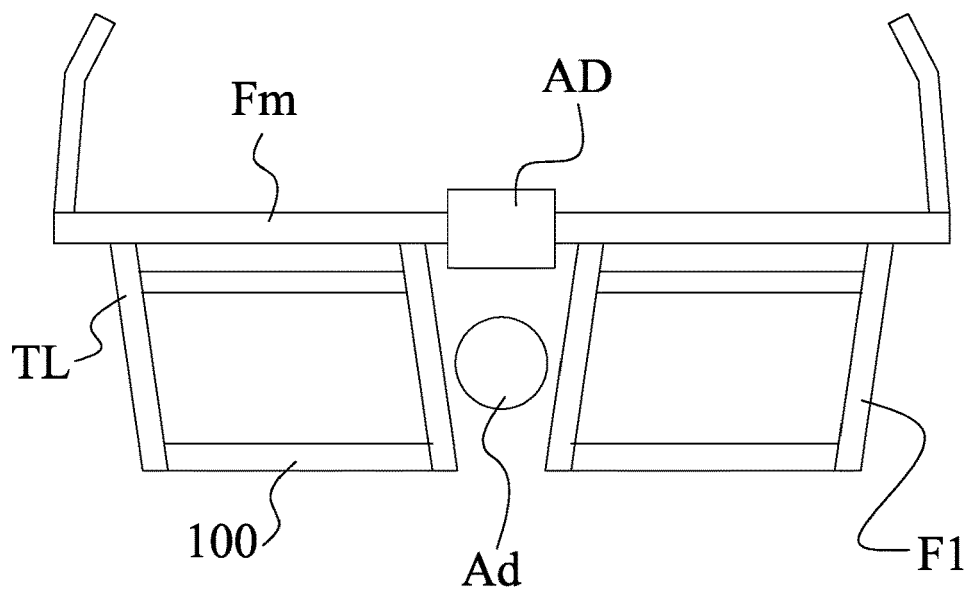
FIG. 20 is top view of the test frame module of the present invention.

Split plate switching test distance knob Ad: using to test distance, split hole plate and pupil distance, binocular split hole plate distance, use a similar triangle formula to calculate the binocular pupil distance (PD) and the corresponding split hole plate distance, so that the split plate is closer and when pushing far, the visual axis of the tester and the optical axis of the corrective lens can be on the same axis (as shown in FIGS. 11, 20).

Visual mark module G: adopt the direction of the corresponding split plate and the size of the corresponding rangefinder.

Ranging module D: measure the distance between the subject and the visual mark.

CCD camera: through photography to assist optometrists to observe whether the eyes of the subject are checked in accordance with the expected instructions. Assist the inspected person to quickly enter into the tested environment.

The binocular vision focal length detection auxiliary device of the present invention, and the second system includes:

1. Interpupillary distance conversion system: Record the test distance and actual interpupillary distance (PD), and convert them as needed.
2. The long and retractable mirror feet system: increase the possibility of wearing different face shapes.
3. The height of the nose pads can be adjusted to increase the possibility of wearing different face shapes.
4. The end of the temples can be straightened or bent to increase the possibility of wearing different faces.
5. The line of sight measurement holes are elongated holes, pinholes, optical measurement holes or horsepower mirrors.

Figure 21:
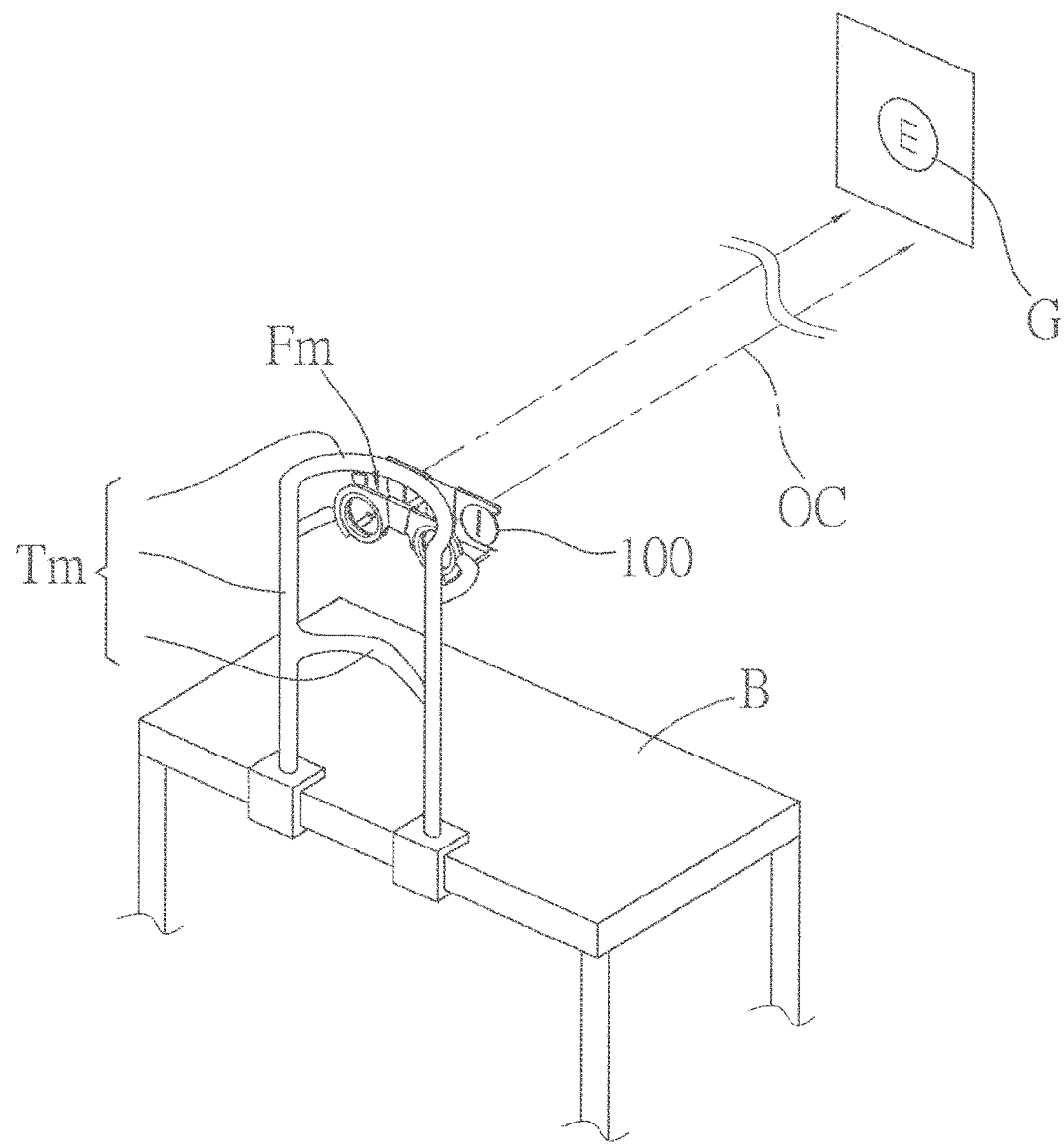
FIG. 21 is a schematic diagram of the test frame of the fixed bracket of the present invention.

The binocular vision focal length detection auxiliary device of the present invention has a fixed bracket Fm matching the system module: in order to increase the stability of the test, the system test frame can be installed in a spectacle-type trial frame, a comprehensive optometry test and a desktop trial frame and erected on the fixed seat B (as shown in FIG. 21).

The experimental results and analysis of the binocular vision focal length detection auxiliary device of the present invention: according to the research motive and purpose, in accordance with the existing optometry process of the optometrist, after the optometry method is completed or the lens is assembled, the system performs consciously The reverse verification of, obtains the final interpupillary distance (PD) and the two geometric center distance (FPD) data of the frame. Wearing based on this data can enhance the fusion of binocular vision and make the subject feel more comfortable after wearing.

Figure 22:
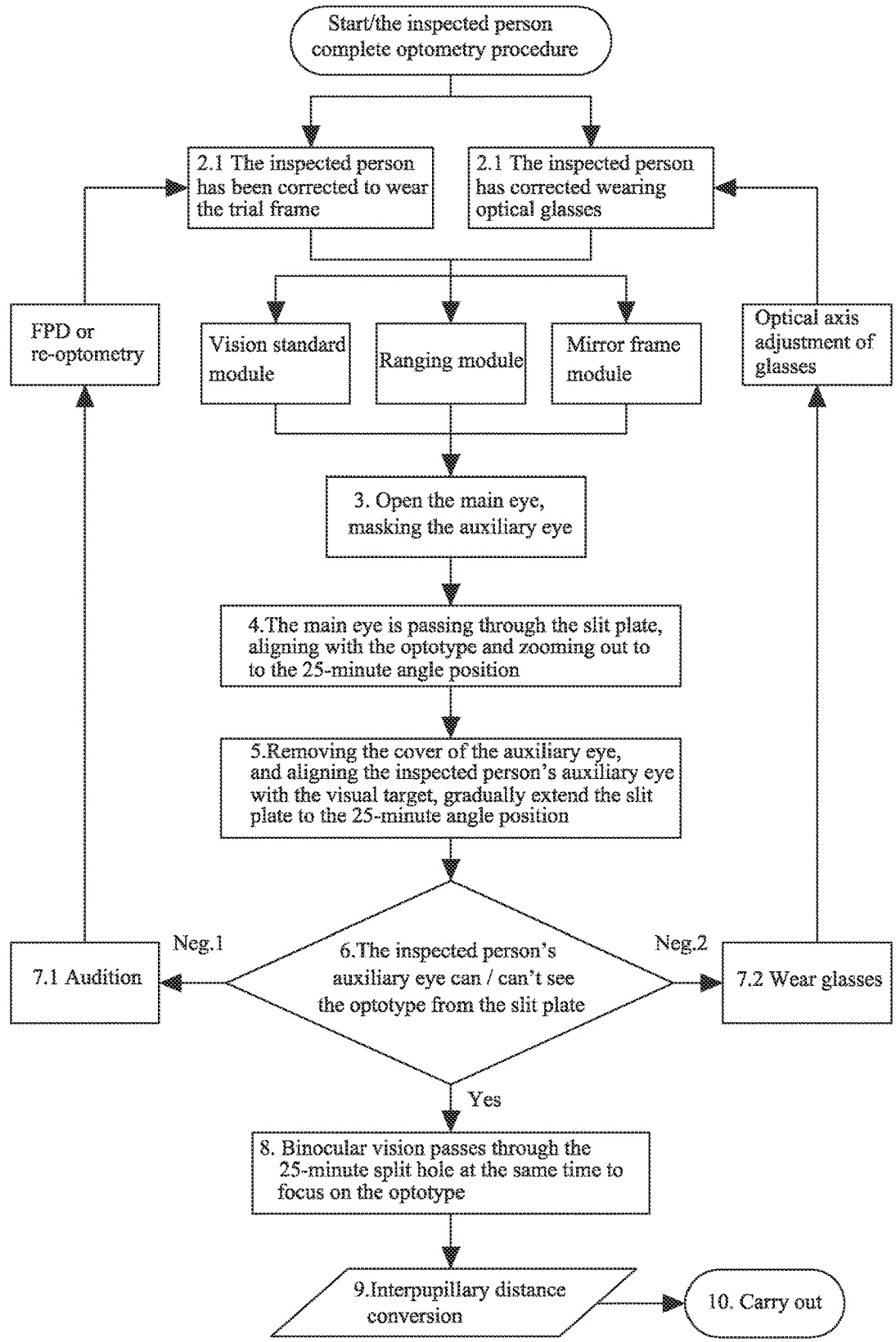
FIG. 22 is a flowchart of the self-conscious PD and fusion inspection of the present invention.

In the binocular vision focal length detection auxiliary device of the second inspection process of the present invention, the inspection steps and the experimental process are divided into ten steps, as shown in FIG. 22, which is briefly described as follows:

1. At the beginning, the inspected person has completed the complete refraction procedure and corrected the refractive error. Those whose vision cannot be corrected to normal condition cannot accept this test.
2. The inspected person will be given trial frames to correct refractive errors temporarily after refraction or the inspected person has worn glasses for correcting refractive errors.
3. Through the construction of this system, the inspected person is asked to open the main eye and cover the auxiliary eye. Because the nerve impulse of the main eye is stronger than the auxiliary eye when it enters into the brain, it will reduce the probability that the binocular vision cannot be found during the examination.
4. The inspected person mainly sees through the slit hole of the slit plate, aligns the visual mark and zooms out to 135 mm, which is a 25-minute angle position. At this time, confirm that the visual mark can still be seen from the crack hole and inform the inspected person to remove the cover of the auxiliary eye.
5. After removing the cover of the auxiliary eye and aligning the inspected person's auxiliary eye with the visual mark, gradually extend the slit plate to the 25-minute angle position, and remind the inspected person that the main eye is still fixed on the visual mark after moving.
6. In the inspection process of step 5, under the requirement of the main eye to fix the visual mark, ask the inspected person's auxiliary eye to confirm whether the visual mark can still be seen from the slit in the process of extending the slit plate. If possible, go to step 8. If not, it means that the preset FPD does not meet the inspected person, go to step 7.
7. For the inspected person in one of the above conditions, please confirm the direction of the auxiliary eye deviation. If the deviation is on the same side, reduce the FPD of the trial frame for myopia patients, and increase the FPD of the frame for hyperopia patients; if the offset is too large, it means that step 1 optometry is not confirmed or the final binocular balance test of optometry is not completed.
8. That is, the binocular vision passes through the 25-minute angle hole at the same time to focus on the visual mark, which means that the binocular fusion is good.
9. Record the test distance, and use the final split plate spacing to convert to the correct FPD and actual interpupillary distance (PD).
10. Complete data analysis.

Figure 30:
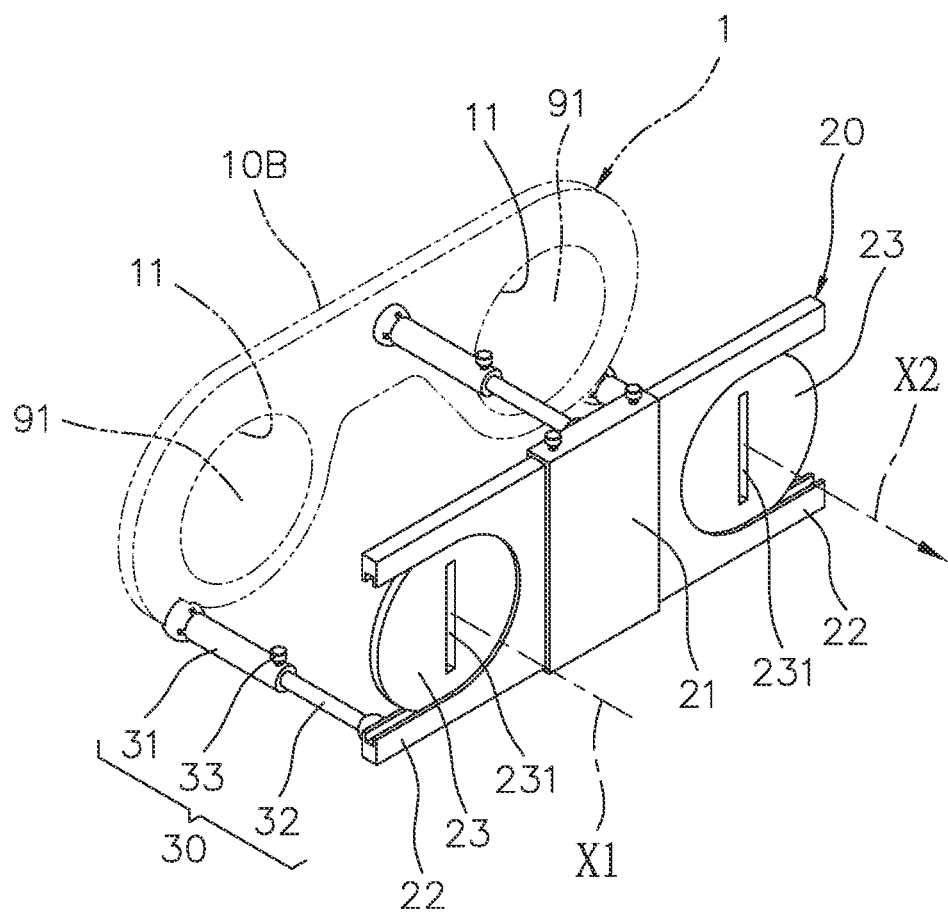
FIG. 30 is a schematic diagram of the optical main frame of the binocular vision focal length detection auxiliary device of the present invention.
Figure 31:
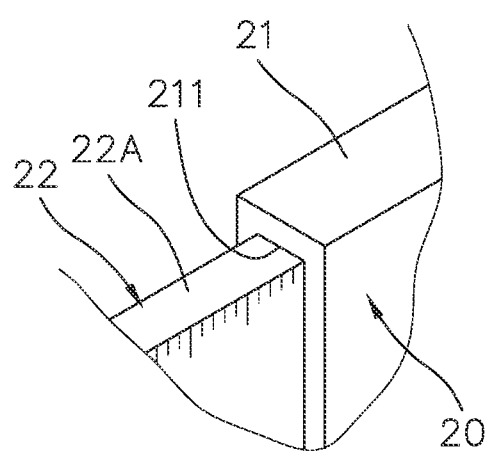
FIG. 31 is a schematic diagram of an application example of the relative position of the insertion end and the frame slot of the binocular vision focal length detection auxiliary device of the present invention, and a ruler is set to measure the relative horizontal movement adjustment distance.

The present invention uses a self-conscious interpupillary distance measuring device using a binocular vision focal length detection auxiliary device, as shown in FIG. 23, FIG. 24A, FIG. 24B and FIG. 25, which includes:

An optical main frame 1, selected from one of the trial frame 10A and general glasses 10B (refer to FIGS. 33A, 33B, and 34);

When selected from the trial frame 10A, it has two circular frame portions 11 and four lens engaging portions 12; the four lens engaging portions 12 are respectively provided on the two round frame portions 11, and are used for Insert at least one lens 91;

When selected from the general glasses 10B (refer to FIG. 30, the temples are omitted and not shown, and are first presented), they have the two round frame portions 11, and each round frame portion 11 is attached the lens 91; each lens 91 is used to correspond to one of the lines of sight X1, X2 of the wearer's eyes 92.

Figure 23:
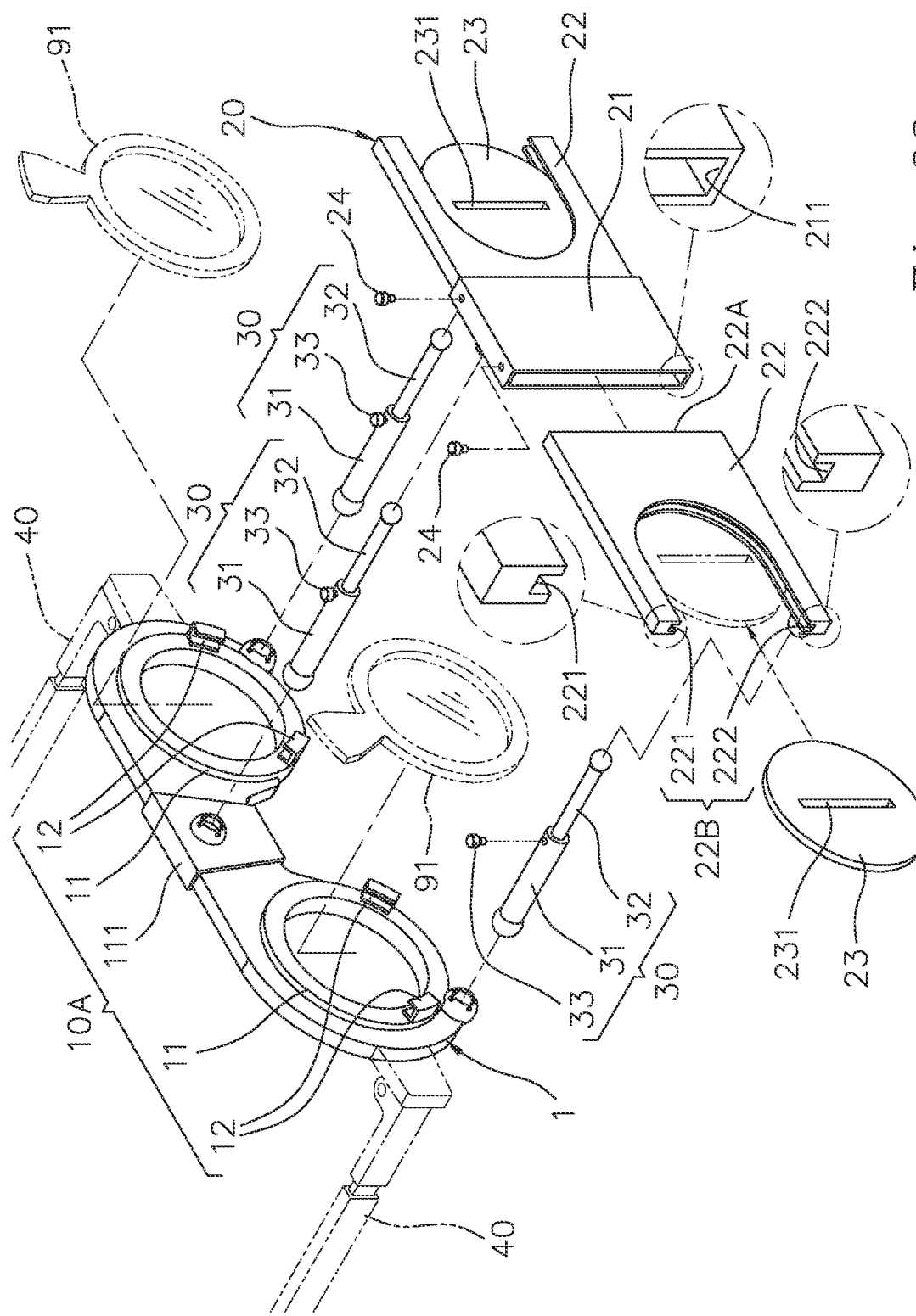
FIG. 23 is an exploded schematic diagram of the binocular vision focal length detection auxiliary device of the present invention.

A pupil sight measuring frame 20 is set corresponding to the optical main frame 1. The pupil sight measuring frame 20 has a body part 21, two movable frame parts 22, two binocular vision focal length detection auxiliary devices 23 and two first fixed part 24. The body portion 21 corresponds to the two movable frame portions 22 and has at least one frame groove 211. Each movable frame portion 22 has an insertion end 22A and an adjustment end 22B facing away from each other. The set end 22A is for the movable frame 22 to be inserted into the frame slot 211, and can be moved and adjusted relative to the horizontal (as shown in FIG. 23, the relative movement can be provided with a ruler, etc., which is easy to distinguish and adjust the distance).

The adjustment end 22B is for the binocular vision focal length detection auxiliary device 23 to be inserted, and can be moved relatively, and can be relatively rotated. The binocular vision focal length detection auxiliary device 23 has a slit 231 corresponding to For one of the sight lines X1 and X2 of the eyes 92, each of the second fixed portions 24 is screwed on the main body portion 21, and when the corresponding movable frame portion 22 and the frame slot 211 are moved horizontally and adjusted to after positioning, the movable frame portion 22 is fixed by a screw lock.

A plurality of telescopic adjustment components 30 are respectively pivoted between the optical main frame 1 and the pupil sight measuring frame 20. Each telescopic adjustment component 30 is used to independently adjust the distance between the optical main frame 1 and the pupil line of sight measuring frame 20 following one of the lines of sight X1 and X2 of the eyes 92.

Figure 29:
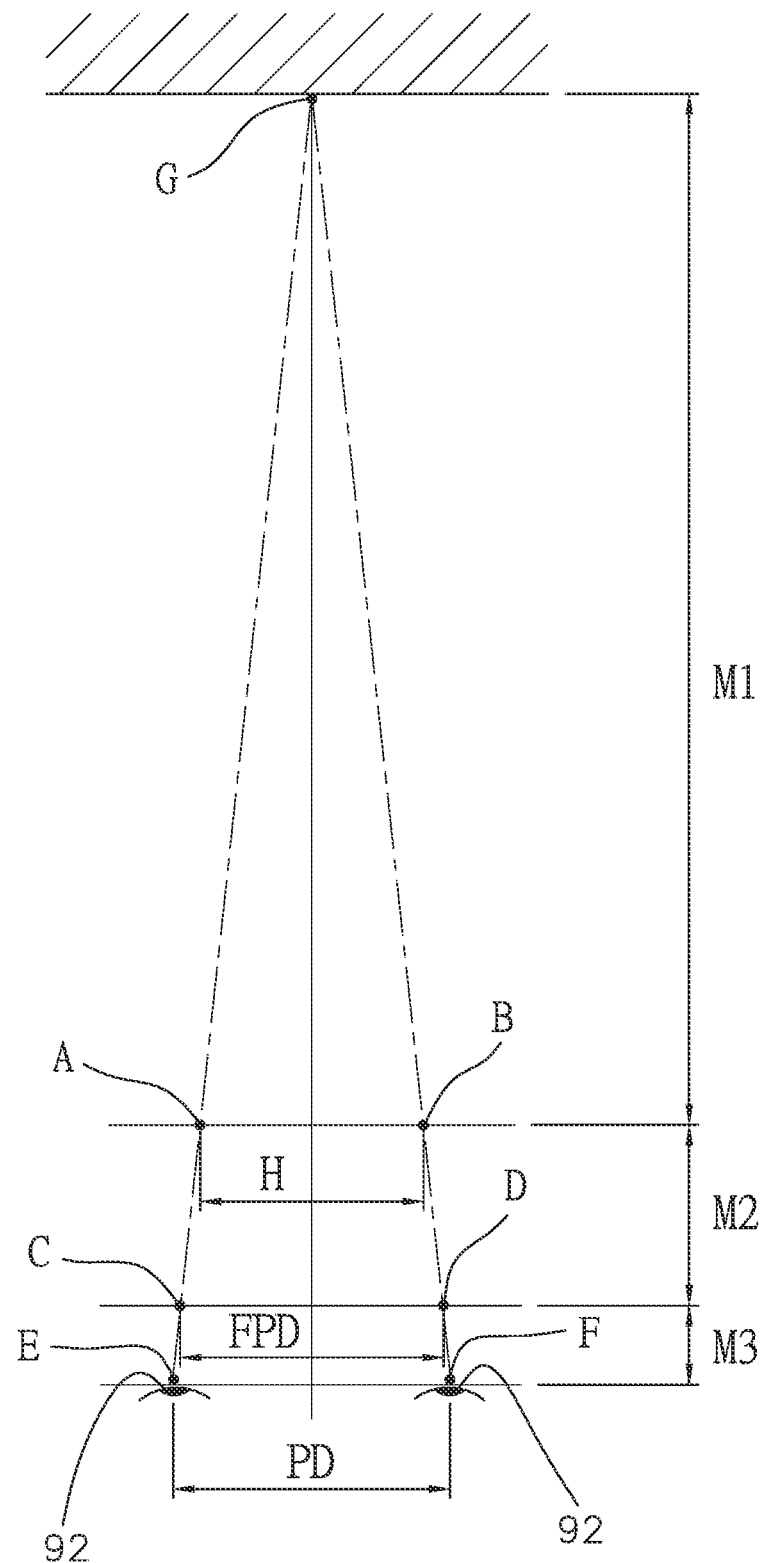
FIG. 29 is a schematic diagram of the correspondence between the components in FIG. 28.

Accordingly, when the line of sight X1, X2 of the eyes 92 of the wearer passes through the at least two lenses 91 and the two slits 231, respectively, viewing an optomark G (as shown in FIG. 29), It is achieved that the pupil distance (PD) of the eyes 92 and the geometric center distance (FPD) of the two circular frame portions 1I can be obtained through calculation of similar triangles.

In practice, the trial frame 10A may further include a central frame 111, and the relatively inner sides of the two round frame portions 11 are inserted into the central frame 111, respectively, and can be adjusted relative to each other (relatively moving for example, a ruler can be set to easily distinguish and adjust the distance, which is not shown in the figure, please be noticed).

Accordingly, the line of sight X1, X2 of each lens 91 corresponding to the eye 92 of the wearer can be adjusted correspondingly.

The trial frame 10A can be at least one of a glasses-type trial frame, a comprehensive refractometer trial frame, and a desktop trial frame.

Figure 26:
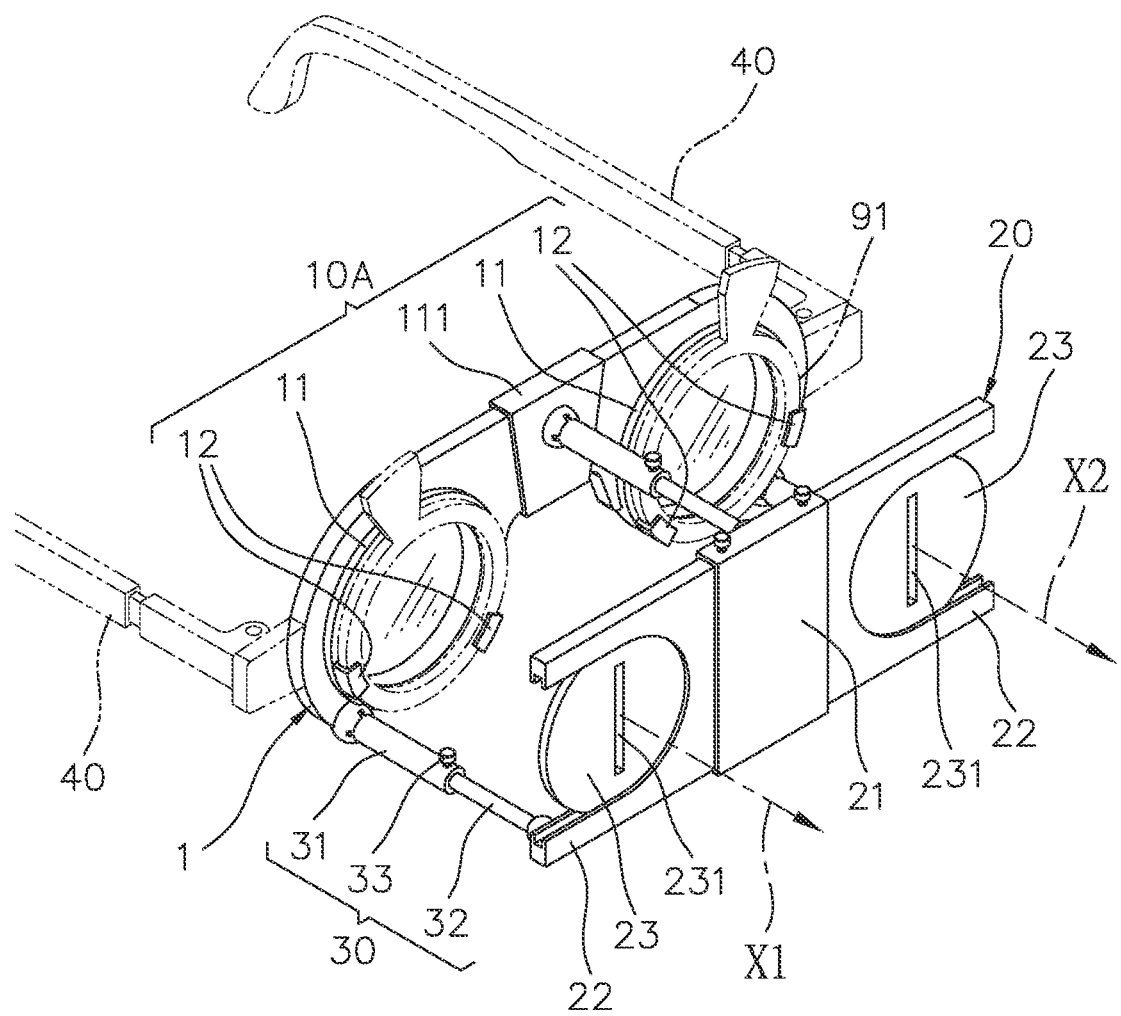
FIG. 26 is a schematic diagram of the first embodiment of the trial frame of the binocular vision focal length detection auxiliary device of the present invention.

When it is a spectacle-type trial frame, it also includes a pair of eyeglass legs 40, which are extended from the trial frame 10A (as shown in FIG. 26) and are opposite to the plurality of telescopic adjustment components 30. The pair of temples 40 are worn by the wearer.

When it is a comprehensive refractometer trial frame, it is only necessary to fix the trial lens frame 10A to a conventional comprehensive refractor, and the fixing method is not limited.

Figure 27:
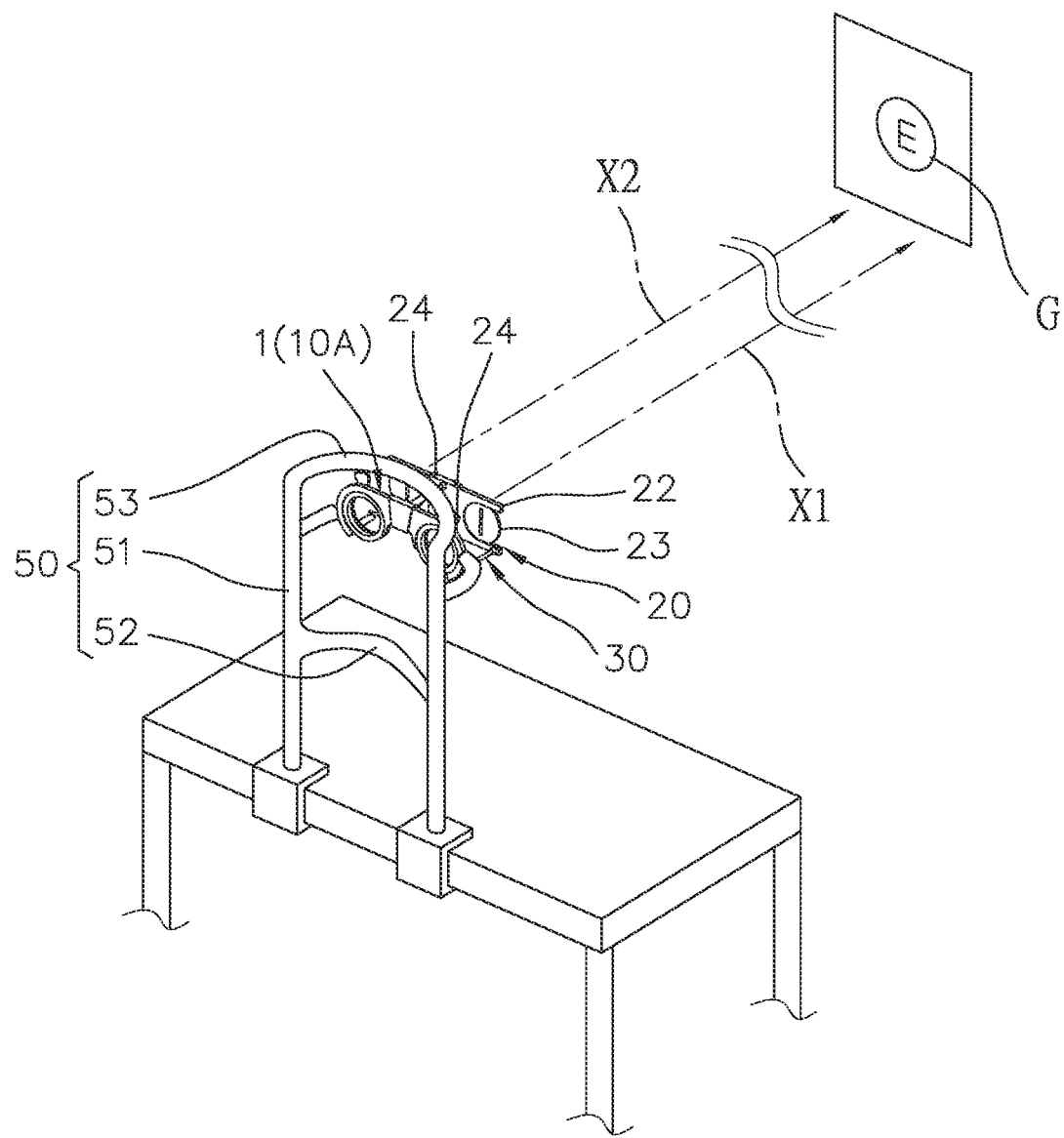
FIG. 27 is a schematic diagram of the second embodiment of the trial frame of the binocular vision focal length detection auxiliary device of the present invention.
Figure 28:
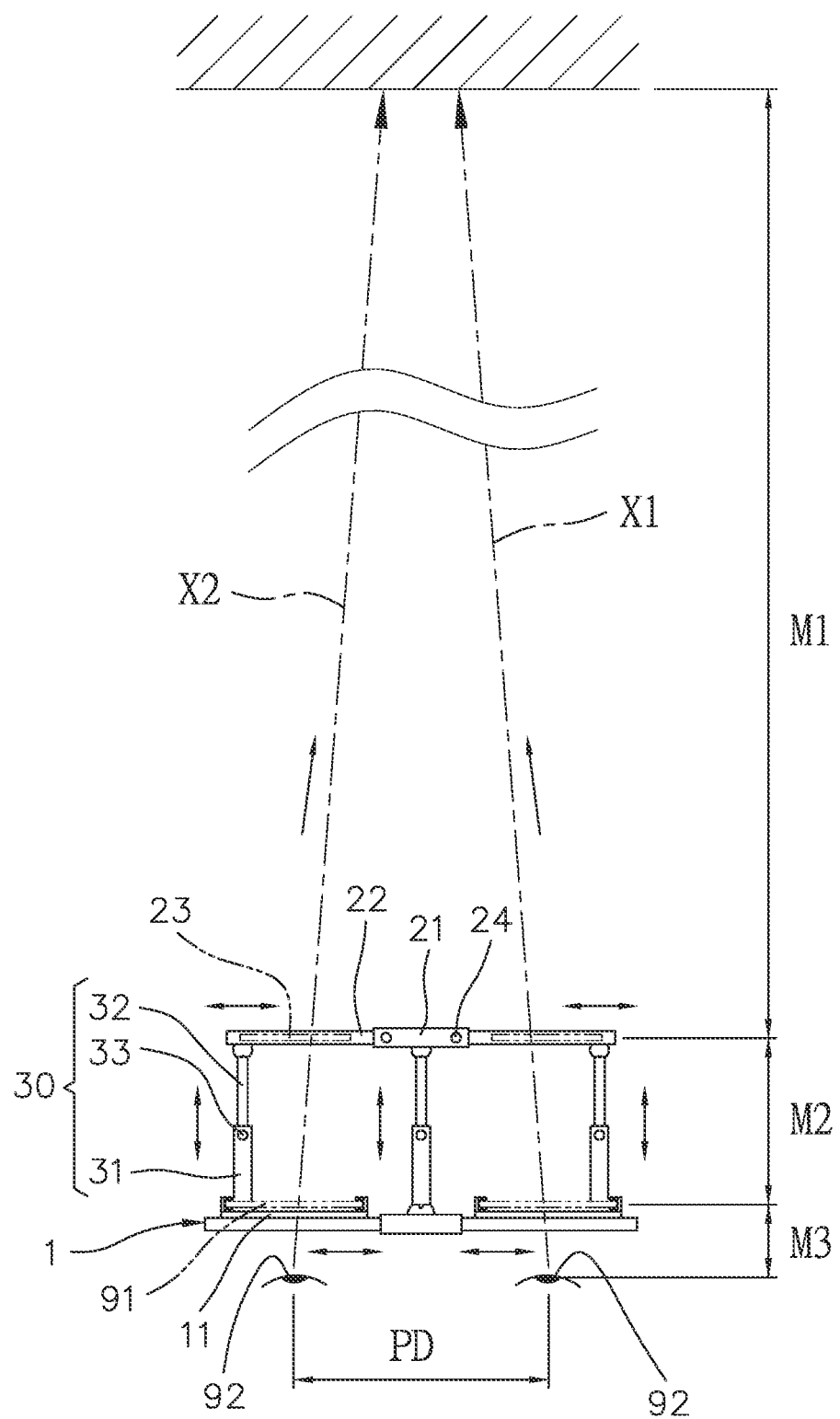
FIG. 28 is a schematic diagram of an application example of the binocular vision focal length detection auxiliary device of the present invention.

When it is a desktop trial frame, it also includes a optometry bracket 50, which is extended from the trial frame 10A (as shown in FIG. 27, the extension or fixing method is not limited), and the plurality of telescopic adjustments The components 30 are opposite to each other. The optometry bracket 50 includes a fixed frame body 51, a chin rest bar 52, and a forehead lever 53. The chin rest bar 52 and the forehead lever 52 are attached to the fixed frame 51 respectively. Extend, respectively, for the inspected person's chin and head to rest.

The frame groove 211 can be one of a single channel structure and a two blind hole structure.

Figure 24A:
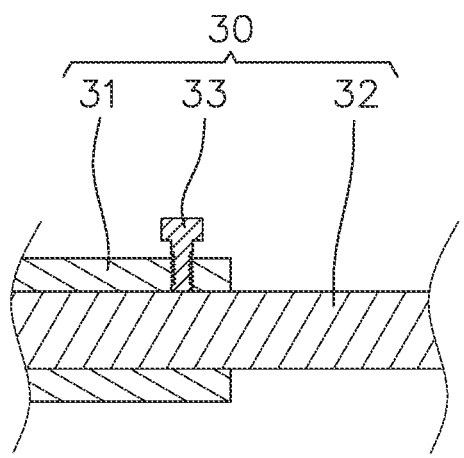
FIG. 24A is a partial cross-sectional view of the telescopic adjustment component of the binocular vision focal length detection auxiliary device of the present invention.
Figure 24B:
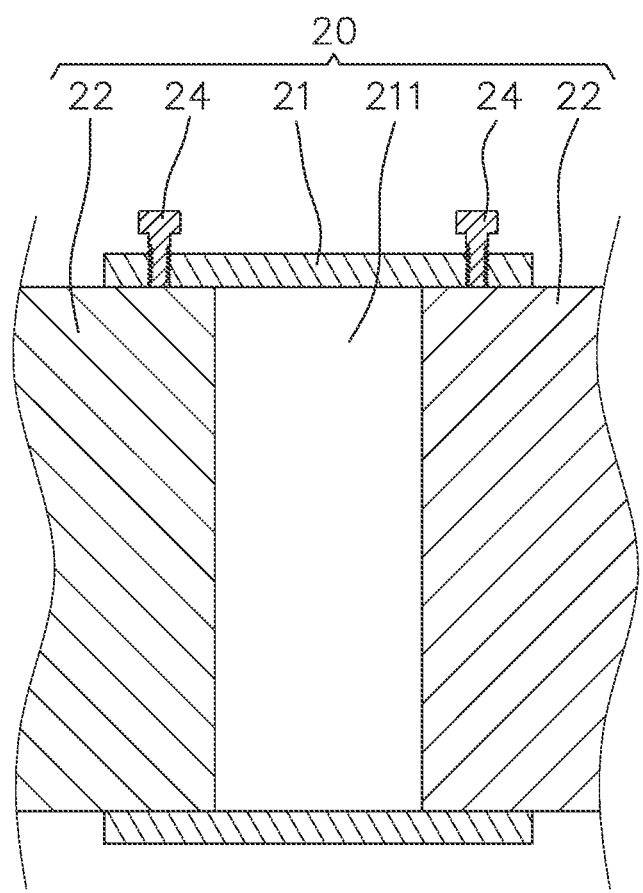
FIG. 24B is a partial cross-sectional view of the pupil line of sight measurement frame of the binocular vision focal length detection auxiliary device of the present invention.
Figure 25:
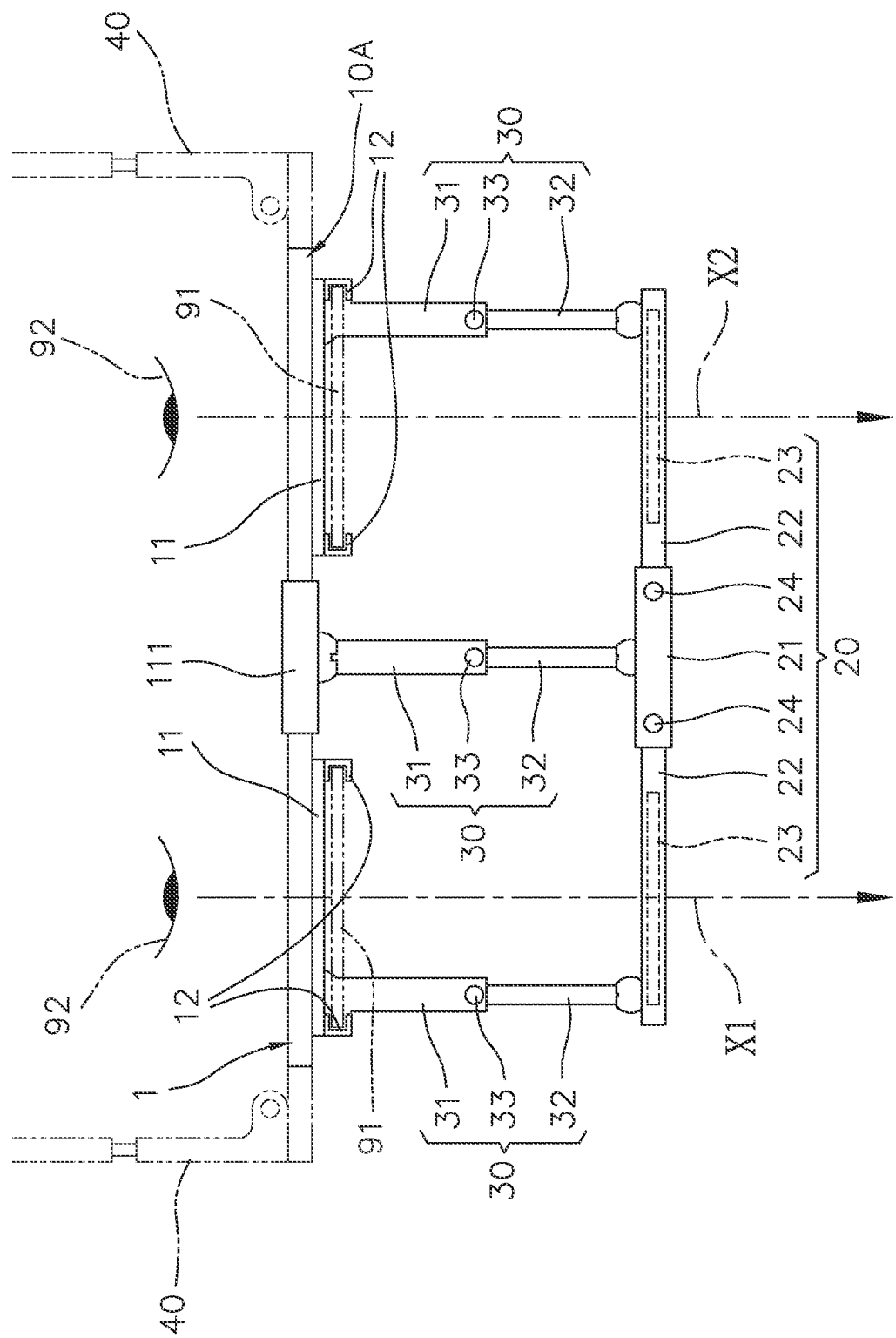
FIG. 25 is a schematic diagram of the correspondence relationship between the binocular line of sight of the binocular vision focal length detection auxiliary device of the present invention and the lens axis together with the slit hole.

When the frame groove 211 is a single-channel structure, it corresponds to the two movable frame portions 22 and penetrates the body portion 21 laterally (as shown in FIG. 24B).

When the frame groove 211 is a blind hole structure, it corresponds to the two movable frame portions 22 and is recessed in the body portion 21 laterally.

Each adjustment end 22B has a corresponding upper groove 221 and a lower groove 222. The upper and lower grooves 221 and 222 are used for the binocular vision focal length detection auxiliary device 23 to be installed and positioned.

The binocular vision focal length detection auxiliary device 23 may be a circular plate corresponding to the upper groove 221 and the lower groove 222.

The binocular vision focal length detection auxiliary device 23 can be a Maddox lens or any one of the same principle optometry structure.

The pupil hole 231 may be one of an elongated hole, a pinhole, and any optical measurement hole of the same principle.

In addition, when receiving an external force (for example, turning with a finger), the binocular vision focal length detection auxiliary device 23 can be rotated in situ to a predetermined angle (rotation of a circular plate is a known technology that can be achieved, and relatively for example, a circular ruler can be set at the rotation position, which is easy to distinguish and adjust the distance. This is a well-known technology, and it is not shown in the drawing, please take a notice of that).

The first fixing portion 24 may be a screw structure.

Figure 32:
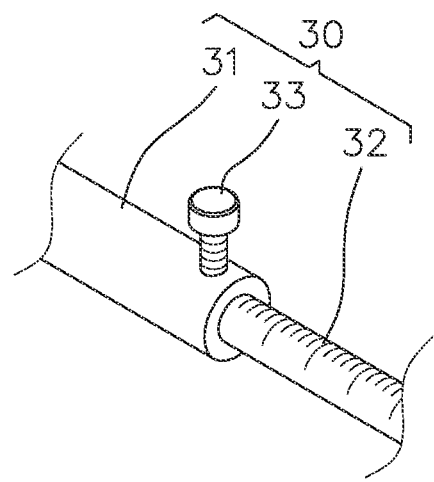
FIG. 32 is a schematic diagram of an application example of the relative position of the telescopic rod part and the fixed pipe part of the binocular vision focal length detection auxiliary device of the present invention.

Each telescopic adjustment assembly 30 may have a fixed pipe portion 31, a telescopic rod portion 32, and a second fixed portion 33. One end of each fixed tube portion 31 is pivotally connected to the optical main frame 1, one end of the telescopic rod portion 32 is telescopically inserted into the other end of the fixed tube portion 31, and the other end of the telescopic rod portion 32 is pivotally connected One of the two movable frame portions 22 of the main body portion 21. The second fixed portion 33 is screwed on the fixed pipe portion 31, when the telescopic rod portion 32 and the fixed pipe portion 31 are telescopically positioned (as shown in FIG. 32, the relative movement can be set, for example, a ruler . . . etc. It is easy to distinguish those who adjust the distance. This is a well-known technology, not shown in the drawing, please aware of that) to fix the telescopic rod 32 with a screw lock.

The second fixing portion 33 may be a screw structure.

In the use process of the present invention, it is assumed that the at least two lenses 91 match (or are quite close, and can be fine-tuned after measurement) the power of the two eyes 92. The wearer wears the binocular vision focal length detection auxiliary device, and the line of sight X1 and X2 of the binocular 92 (see FIG. 25, FIG. 26, FIG. 27 and FIG. 28) pass through the When the lens 91 and the tear hole 231 are looking toward a visual mark G, they begin to measure the interpupillary distance consciously:

First, cover one eye, measure the other opened eye, and then rotate the binocular vision focal length detection auxiliary device 23 corresponding to the opened eye by the wearer. The rotation process must keep the hole through the hole 231 sees the visual mark G, and at least rotates to the two positions of the slit 231 at 180 degrees and 90 degrees (indicated by the matching angle). Of course, the position may be slightly deviated from the visual mark G, at this time, the relevant medical or optometrist can assist in adjusting at least one of the following:

[a] Binocular vision focal length detection auxiliary device adjustment. Control the binocular vision focal length detection auxiliary device 23 and the adjustment end 22B to move or rotate relative to each other, so that the binocular vision focal length detection auxiliary device 23 is moved to the position where the hole 231 is located over one of the sight line X1 or X2.

[b] Adjustment of pupil sight measurement frame. Unscrew the corresponding first fixing portion 24, and control the relative movement of the movable frame portion 22 and the frame groove 211, so that the binocular vision focal length detection auxiliary device 23 is moved until the slit 231 is located at one of the line of sight X1, X2. Tighten the first fixing part 24 again.

[c] Adjust the telescopic adjustment assembly. The corresponding second fixing portion 33 is loosened, the telescopic rod portion 32 and the fixed tube portion 31 are controlled to expand and contract to an appropriate position, and the second fixing portion 33 is tightened again.

After at least one of the aforementioned three adjustment actions, the binocular vision focal length detection auxiliary device 23 rotates to the two positions of the slit 231 at 180 degrees (horizontal) and 90 degrees (vertical), All should be able to see the visual mark G. Repeat the same action to measure the other eye, and when both eyes 92 are opened at the same time, two lines of sight X1 and X2 can be focused on the visual mark G (as shown in FIG. 29). In such a process, the wearer consciously rotates and moves the binocular vision focal length detection auxiliary device 23 to determine its visual center position.

Referring to FIG. 29, at this time the two slits 231 respectively have a sight hole point A and B, and a sight hole distance H between them. The two lenses 91 respectively have a lens axis point C and D, and a lens axis distance FPD (which can also be said to be the geometric center distance of the two circular frame portions 11) therebetween. The two pairs of eyes 92 respectively have a pupil point E and F, and a pupil distance PD therebetween. There is a first distance M1 between the visual mark G and the pupil sight measuring frame 20, and a second distance M2 between the pupil sight measuring frame 20 and the optical main frame 1, and the optical main frame 1 and the eyes There is a third distance M3 between 92, and then through the calculation of similar triangles, the following relationship is produced:

$$GA:H = GC:FPD = GE:PD$$

$$M1:H = (M1+M2):FPD = (M1+M2+M3):PD$$

That is, finally, the pupil distance PD and the distance between the two geometric centers of the two circular frame portions 11 (ie, the lens axis distance FPD) can be estimated and confirmed.

The fusion image of the two eyes 92 can be further improved to make the inspected person's visual experience more comfortable.

In addition, the distance to the center of eyeball rotation can also be calculated in this case. Please refer to FIG. 27. First define the center points J and K of the eyes. Assuming that the visual mark G is a distant visual mark (for example, M1 is 500 cm), after the fusion of the eyes 92 is determined by the aforementioned method, you can record the relevant data;

after that, the original visual mark G is moved to the wearer to become a near visual mark G'. There is a near first distance M1 between the near visual mark G' and the pupil sight measurement frame 20'(Assuming it is 250 cm), after the fusion of the eyes 92 is determined, the relevant data can be recorded;

using the geometric relationship between the triangle GJK and the triangle G'JK, the angle between GA and GB (A and B are sight hole points) can be known from the known M1 and AD; in the same way, from the known M1' and the near sight hole point A' and B', the angle between G'A' and G'B' can be obtained (similarly, the angle between G'C' and G'D' can be obtained from the point C' and D' of the proximal lens axis); using mathematical calculations, the common base JK of triangle GJK and triangle G'JK (that is, the distance from the center of eyeball rotation) can be solved. Therefore, the present application also has the ability to calculate eyeball center rotation. This data is very helpful to the field of optometry.

In addition, by using the technologies of Artificial Intelligence (AI), the present invention calculate the visual comfort of inspected person to the objects of "point, lines, and surfaces". That is, using projection technology to project "points, lines, surfaces" to simulate binoculars; and importing the measured inspected person's eyeball rotation parameters into the system, add the treated optical lenses where consumers buy, and setting in match with the inspected person's environmental conditions.

Figure 33:
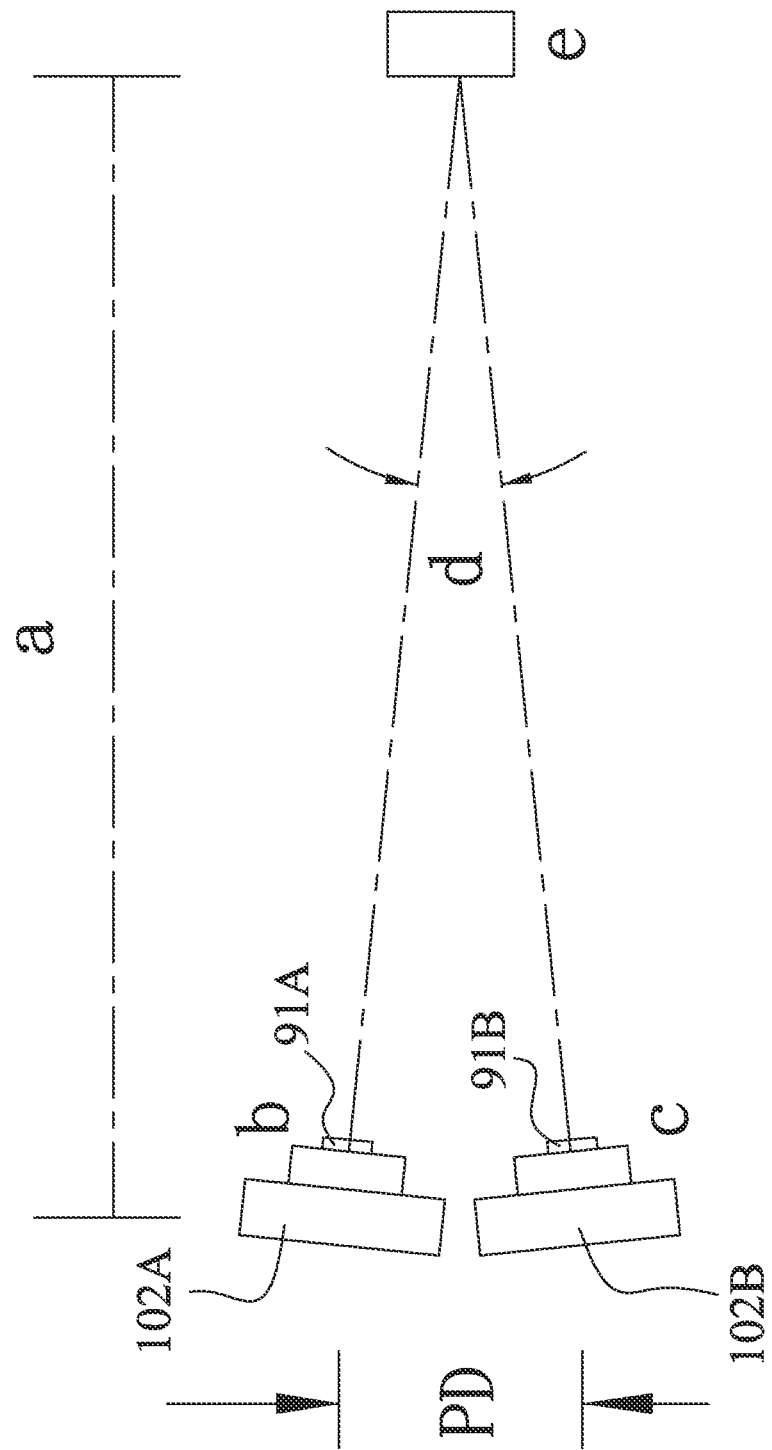
FIG. 33 is an explanatory diagram showing the obtained of best lens fit point by using AI calculation of the present invention.

While as shown in FIG. 33, the best fit point of AI calculations for lens includes the following parameters.
(a) Distance of use environment
(b) Simulate left eye projection
(c) Simulate right eye projection
(d) Light angle
(e) Imaging verification of points, lines and surfaces.

Please refer to FIG. 3, FIG. 11, FIG. 27, FIG. 28, FIG. 29 and FIG. 33, if projector 102 of FIG. 3 is replaced by includes right and left projectors 102A and 102B shown in FIG. 33 for simulated projections are respectively fitted onto a multi-directional joint and a telescopic mechanism, then the simulated eyes are form. Thus by the images e projected by projectors 102A, 102B through lenses 91A, 91B onto the screen, the further parameters for adjusting lenses are obtained.

The advantages and effects of the second process of the present invention are as follows:

[1] The conscious interpupillary distance measurement is more in line with the actual visual experience of the lens wearer. The subject process is provided with an adjustable optical main frame, pupil sight measuring frame and telescopic adjustment assembly. After adjustment of each element, the lens wearer can consciously and clearly see the visual mark through the slit during the rotation with his own line of sight, And then record the adjusted data of each element, and cooperate with the installation and adjustment of the lens on the frame, which can better present the data at the time of optometry, thereby improving the comfort of wearing glasses.

[2] No expensive equipment is required, and the cost is low. The subject process is composed of general optometry equipment (such as optical main frame and lenses) and a simple support structure (pupil sight measurement frame and telescopic adjustment component). There is no complicated electronic equipment and no complicated operation steps. As long as a optimist guide the lens wearer to use.

[3] The distance to the center of eyeball rotation can be calculated. As long as two operations (a farther and a near vision target), the geometric relationship between the two triangles can be used to calculate the distance to the center of eye rotation through mathematical calculations, which is very helpful for the field of optometry.

However, the above are the preferred specific embodiments of the present invention. If changes are made according to the concept of the present invention, and the resulting functional effects do not exceed the spirit covered by the specification and illustrations, they should be within the scope of the present invention, it has to be well stated.

What is claimed is:

1. A vision inspection and correction method, includes two inspection processes and systems, a first one of the two inspection processes being an image fusion process, and a second one of the two inspection processes being a binocular vision focal length detection process;

wherein the first one comprises a step of using an adjustment device to perform at least one of enlarging, reducing, shifting, focusing, diverging and rotating a misaligned image obtained by an inspected person's abnormal eyes, so that the inspected person's eyes can see an aligned image projected on a display screen, wherein the adjustment of the misaligned image to the aligned image by the image adjustment device generates adjustment data which can be converted into correction data of a glasses, such that a lens maker is enabled by the correction data to make a lens for the inspected person to see the aligned image through the lens;

wherein a display screen is used to display images, such that both eyes of the inspected person can see a convergence on the display screen, and the inspected person can see a fusion image with a single eye and separate the images;

wherein a projection equipment is connected with a central processing unit (CPU), and accepts image files stored in the central processing unit to project the image onto the display screen, the image stored in the central processing unit (CPU) has an independent three-dimensional image, including images of points, lines, and planes, wherein the separated images can be respectively seen by left and right eyes; and wherein a remote control is used to control the the projection equipment, and the projected image is adjusted by enlargement, reduction, shifting, focusing, diverging or rotation of an instruction received from the inspected person.

2. The visual inspection and correction method as claimed in claim 1, the three-dimensional visual inspection steps are as follows:

Step 1: project the image from the central processing unit (CPU) to the display screen; the image is a combination of two halves of the image, which is for the subject with normal eyes in terms of seeing an aligned fusion image;

Step 2: if the image seen by the subject's eyes is a non-aligned fusion image, the subject is asked to look at the image with a single eye one by one, and use the remote control or keyboard (mouse) zoom in or zoom out the images one by one: shift left/right or up/down; focus or diverge; turn left/right; turn up/down, etc., until the subject's eyes see the image is up to the aligned fusion;

Step 3: the adjusted data obtained in step 2 is a correction parameter, and the correction parameter is sent to the lens maker to produce lens suitable for the inspected person to wear.

3. The vision detection and correction method as claimed in claim 1, using a binocular image separation device equipment that can see different images on the X, Y, and Z axes simultaneously, comprising:

A. using the binocular image separation device that can see different images on the X, Y, and Z axes simultaneously;

B. performing an XY-axis fusion test of X, Y, and Z axes, use the independent imaging method of both eyes to let the left eye look at a first mark and the right eye to look at a second mark, then using a regulator to adjust the size of the X-axis of non dominant eye to conform with the size to the X-axis of dominant eye; then rotating the optomark 90 degrees around the Z axis to adjust the size of Y-axis of non dominant eye to conform with the size of the Y-axis of dominant eye, thus the image difference parameters of the XY axis of the inspected person's eyes can be obtained;

C. performing an XZ axis fusion test of X, Y, and Z axes, use the binocular independent imaging method to allow the left eye to look at the first mark and the right eye to look at the second mark, then using a regulator to adjust the size of the X-axis of non dominant eye to conform with the X-axis of dominant eye; then rotating the optomark 90 degrees around the Y axis to adjust the size of the Z-axis of non dominant eye to conform with the size of the Z axis of dominant eye, then image difference parameters of the XZ axis of the inspected person's eyes can be obtained;

D. performing an ZY-axis fusion test of the X, Y, and Z axes, use the binocular independent imaging method to allow the left eye to look at the first mark and the right eye to look at the second mark then using a regulator to adjust the size of Z-axis of the non dominant eye to conform with the Z-axis of dominant eye; then rotating the optomark 90 degrees around the X axis to adjust the size of Y-axis of non dominant eye to conform with the size of the Y axis of dominant eye, thus the image difference parameters of the ZY axis of the inspected person's eyes can be obtain;

E. wherein the XY, XZ, and ZY three-plane spatial difference parameters of the inspected person are made into a dual-eye separation imaging device, which can correct the physiological and optical errors of the human eye with the two dimensional image or three-dimensional image.

4. The vision detection and correction method as claimed in claim 1, the binocular vision focal length detection process uses auxiliary device including:

an optical main frame with two round frame parts, the round frame part can be used to put lenses;

one pupil line of sight measurement frame, with two movable frame parts;

two binocular vision focal length detection auxiliary devices, which are respectively arranged on the movable frame part of the above-mentioned pupil line of sight measurement frame and are rotatable, and have a slit corresponding to the line of sight of a lens wearer;

at least one telescopic adjustment component, pivotally arranged between the optical main frame and the pupil sight measuring frame, and can be used to adjust the distance between the optical main frame and the pupil sight measuring frame;

thereby, when the lens wearer wears the optical main frame, the line of sight can pass through the aperture of the lens and the binocular vision focal length detection auxiliary device to view an optotype, and through the calculation of similar triangles obtain the distance between the pupil of the eye and the distance between the two geometric centers of the two circles can be obtained.

5. The vision detection and correction method as claimed in claim 4, wherein the frame groove of the main body part can be a single-channel structure or a two-blind hole structure; the movable frame part penetrates the main body part laterally; when it has a two blind hole structure, it corresponds to the two movable frame parts and is recessed in the main body part laterally;

wherein the adjustment end of the movable frame part has a corresponding upper groove and a lower groove; the upper groove and the lower groove is used to provide the binocular vision focal length detection auxiliary device for installation and positioning; the binocular vision focal length detection auxiliary device is a circular plate corresponding to the upper groove and the lower groove.

6. The vision detection and correction method as claimed in claim 4, said projection device for points, lines and surfaces is replaced by right and left projectors for simulated projections are respectively fitted onto a multi directional joint and a telescopic mechanism, then the simulated eyes are formed, thus by the images projected by said right and left projectors through lenses onto the screen, further parameters for adjusting said lenses are obtained.

7. The visual inspection and correction method as claimed in claim 1, wherein an auxiliary device is used, which is at least a plate with a slit, when performing visual inspection, set the plate in front of the inspected person's eyes, the inspected person can see through the slit and see a front visual mark, and the condition of the target is communicated to an examiner, so as to obtain information about the ability of the inspected person's eye to focus; the slit can be a long strip hole, a pinhole or an optical measuring hole, which can follow a binocular vision focal length detection auxiliary device rotation to a predetermined angle.

8. The vision detection and correction method as claimed in claim 7, wherein the pupil line of sight measuring frame is further provided with a main body and a first fixed part; the main body part has frame grooves corresponding to the two movable frame parts, each movable frame portion has an insertion end portion and an adjustment end portion facing each other, and the insertion end portion provides the movable frame portion to be inserted in the frame groove, and can be moved and adjusted relatively horizontally; its adjusting end provides the binocular vision focal length detection auxiliary device to be moved or rotated after being inserted; when the corresponding movable frame portion and the frame groove are moved horizontally and adjusted to position, the first fixed portion is fixed.

9. The vision detection and correction method according to claim 1, wherein, the measured telescopic adjustment component of said auxiliary device has a fixed tube portion, a telescopic rod portion and a second fixed portion; one end of the fixed tube portion is pivotally connected to the optical main frame, one end of the telescopic rod part is telescopically inserted into the other end of the fixed tube part, and the other end of the telescopic rod part is pivotally connected to one of the two movable frame parts of the main body part; after the telescopic rod part and the fixed tube part are stretched to a position, the second fixed part is screwed and fixed.

* * * * *